US008741324B2

(12) United States Patent
Finch et al.

(10) Patent No.: US 8,741,324 B2
(45) Date of Patent: Jun. 3, 2014

(54) LIQUID PESTICIDE COMPOSITIONS

(75) Inventors: Charles W. Finch, Garner, NC (US);
Thomas Byrne, Chapel Hill, NC (US);
Hassan Oloumi-Sadeghi, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 910 days.

(21) Appl. No.: 11/631,462

(22) PCT Filed: Jul. 5, 2005

(86) PCT No.: PCT/EP2005/007256
§ 371 (c)(1),
(2), (4) Date: Jan. 3, 2007

(87) PCT Pub. No.: WO2006/002984
PCT Pub. Date: Jan. 12, 2006

(65) Prior Publication Data
US 2007/0184983 A1   Aug. 9, 2007

Related U.S. Application Data

(60) Provisional application No. 60/585,073, filed on Jul. 6, 2004.

(51) Int. Cl.
| | | |
|---|---|---|
| A01N 25/02 | (2006.01) | |
| A01N 33/26 | (2006.01) | |
| A01N 37/22 | (2006.01) | |
| C07C 233/65 | (2006.01) | |
| C07C 233/80 | (2006.01) | |
| C07C 237/00 | (2006.01) | |
| C07C 243/18 | (2006.01) | |
| C07C 245/04 | (2006.01) | |
| C07C 251/06 | (2006.01) | |
| C07C 251/86 | (2006.01) | |
| C07C 275/28 | (2006.01) | |
| C07C 275/30 | (2006.01) | |
| C07C 281/10 | (2006.01) | |
| C07C 281/14 | (2006.01) | |

(52) U.S. Cl.
USPC .......... 424/405; 504/100; 504/310; 504/312; 504/334; 504/336; 514/613; 514/615; 564/123; 564/148; 564/149; 564/181

(58) Field of Classification Search
USPC .................. 424/405; 504/310, 312, 334, 336; 514/613, 615; 564/123, 148, 149, 181
See application file for complete search history.

(56) References Cited

U.S. PATENT DOCUMENTS

| | | | | |
|---|---|---|---|---|
| 4,851,217 A | * | 7/1989 | Mente | 525/356 |
| 5,420,165 A | | 5/1995 | Furch et al. | |
| 5,543,573 A | * | 8/1996 | Takagi et al. | 514/590 |
| 2007/0020304 A1 | * | 1/2007 | Tamarkin et al. | 424/405 |
| 2008/0300313 A1 | * | 12/2008 | Byrne et al. | 514/611 |

FOREIGN PATENT DOCUMENTS

| | | | | |
|---|---|---|---|---|
| EP | 0 209 462 | 1/1987 | | |
| EP | 0 302 701 | 2/1989 | | |
| EP | 0 427 582 | 5/1991 | | |
| JP | 05004958 | 1/1993 | | |
| JP | 6293605 | 10/1994 | | |
| JP | 7-285803 | 10/1995 | | |
| JP | 11501630 | 2/1999 | | |
| WO | WO 88/07326 | * 10/1988 | ............. | A01N 25/04 |
| WO | WO 88/09122 | 12/1988 | | |
| WO | WO 90/03112 | 4/1990 | | |
| WO | WO 92/10937 | 7/1992 | | |
| WO | WO 96/27290 | 9/1996 | | |
| WO | WO88/09122 | * 12/1998 | ............. | A01N 25/30 |
| WO | WO 02/45507 | 6/2002 | | |
| WO | WO 03/037084 | 5/2003 | | |

\* cited by examiner

*Primary Examiner* — Jane C Oswecki
(74) *Attorney, Agent, or Firm* — Brinks Gilson & Lione

(57) ABSTRACT

The present invention relates to liquid pesticide concentrate compositions which comprise at least one organic pesticide compound that is sparingly or even insoluble in water and which upon dilution with water form stable aqueous nanoparticulate formulations. The liquid pesticide concentrate compositions of the invention comprise: a) at least one organic pesticide compound C having a water solubility of not more than 1 g/l at 25° C./1013 mbar, b) at least one organic solvent S having a water solubility at least 10 g/l at 25° C./1013 mbar, and which is capable of dissolving the pesticide compound C, or a mixture of at least one organic solvent S with water, provided that the weight ratio of water to solvent S does not exceed 1:2, c) at least one non-ionic blockcopolymer P comprising at least one polyethyleneoxide moiety PEO and at least one hydrophobic polyether moiety consisting of repeating units selected from $C_3$-$C_{10}$-alkyleneoxides and styrene oxide, d) optionally one or more non-polymeric surfactants, wherein the weight ratio of the non-ionic blockcopolymer to the organic pesticide compound P:C is from 0.6:1 to 10:1 and wherein the components a), b) and optionally d) make up at least 95% of the composition. The invention also relates to aqueous pesticide compositions which are obtained by diluting the concentrate pesticide compositions of the invention with water and to their use for plant protection.

31 Claims, No Drawings

LIQUID PESTICIDE COMPOSITIONS

This application is a National Stage application of International Application No. PCT/EP2005/007256 filed Jul. 5, 2005, which claims the benefit of U.S. Provisional Application No. 60/585,073, filed Jul. 6, 2004, the entire contents of which is hereby incorporated herein by reference in its entirety.

The present invention relates to liquid pesticide compositions which comprise at least one organic pesticide compound that is sparingly or even insoluble in water and which upon dilution with water form stable aqueous nanoparticulate formulations. The invention also relates to aqueous pesticide compositions which are obtained by diluting the non-aqueous pesticide compositions of the invention with water and to their use for plant protection.

A pesticide compound, hereinafter also referred to as active ingredient, is usually applied in the form of a dilute aqueous composition in order to achieve a good interaction with the target organisms, such as plants, fungi and insects. However, most active ingredients that are used as pesticides are only sparingly or even insoluble in water, i.e. they usually have a water-solubility of not more than 1 g/l, often not more than 0.5 g/l and particularly not more than 0.1 g/l at 25° C./1013 mbar. Therefore, formulators are often confronted with difficulties in formulating pesticide compounds in stable formulations that can be easily diluted with water and that deliver maximum loading of the active ingredient per unit volume to the end user.

Pesticides having a low solubility in water are often formulated as aqueous suspension concentrate (SC) which can be diluted with water for use in the field. Suspension concentrates are formulations, wherein the active ingredient is present in the form of finely divided solid particles, which are suspended in an aqueous dispersing medium utilizing surface-active compounds, such as wetting agents, dispersants and rheological or suspending aids for stabilising the active ingredient particles in the dispersing medium. In SC's, the particles of the active ingredient usually have particle sizes in the range of 1 to 20 μm. Even smaller particle sizes, i.e. <1 μm, e.g. 0.5 to <1 μm, can be obtained by elaborate grinding techniques. However, problems are often encountered with SC's as a result of settling during prolonged storage or storage at elevated temperatures, the resistance of settled particles to re-suspension and the formation of crystalline material upon storage. As a consequence, the formulations are difficult to handle and the bioefficacy may be inconsistent. Moreover, since the particle size of the active ingredient particles is large in SC's, it may often result in a lower efficacy.

An alternative for formulating water-insoluble active ingredients are so-called emulsifyable concentrates (EC). In an EC the active ingredient is dissolved in a water-immiscible solvent (solubility usually <0.1 g/l), such as an aromatic hydrocarbon, together with surface-active ingredients. EC's are usually stable solutions that can be diluted with water to form a milky oil-in-water emulsion, containing the active ingredient dissolved in the solvent droplets. EC formulations have a considerable drawback in that they contain considerable amounts of volatile organic solvents which are not entirely satisfactory with regard to their ecological and toxicological properties. Moreover, EC's are limited to pesticide compounds which are soluble in water-immiscible solvents. As a result of the large particle size of the solvents droplets, the bioefficacy of the active ingredient is sometimes not satisfactory.

WO 92/10937 suggests a pesticide concentrate which comprises a solid water-insoluble pesticide compound and a dispersant which is solubilized in a water-miscible solvent in order to overcome the problems associated with SC's and EC's. Upon dilution with water, these formulations form a suspension of finely divided active ingredient particles. However, the active ingredient is often rapidly precipitated as coarse crystals giving both application problems, such as spray filter or nozzle blockage and poor or inconsistent bioefficacy. Moreover, loading of these compositions with an active ingredient is poor and the particle size of the active ingredient after dilution with water is not entirely satisfactory.

WO 03/037084 describes a similar concentrated pesticidal solution which comprises one or more water-insoluble pesticide compounds and lignin dissolved in a water-miscible, polar solvent. Depending on the active ingredients choice, it may be rapidly precipitated giving coarse crystalline particles. Thus the active ingredients have inconsistent bioefficacy and application problems are likely to occur.

WO 02/45507 describes a concentrate composition of a hydrophobic pesticide compound, wherein the active ingredient and at least one surfactant are dissolved in a solvent system comprising hydrophobic, water insoluble alkylalkanoates as a first solvent and polyhydric alcohols or condensates of polyhydric alcohols as a second solvent. The compositions require a hydrophobic, water insoluble solvent which is undesirable.

Therefore, it is an object of the present invention to provide a stable concentrate formulation for organic pesticide compounds having a water-solubility of not more than 5 g/l, in particular not more than 1 g/l or even not more than 0.5 g/l at 25° C./1013 mbar. Upon dilution with water, the formulation should form a stable aqueous composition of the active ingredient, wherein the average particle size of the dispersed material should not exceed 0.5 μm, preferably 300 nm and in particular 200 nm. Moreover, the formulation should not form coarse material upon dilution with water and the active ingredient should be stable in the liquid concentrate formulation upon prolonged storage or storage at elevated temperatures. Moreover, the aqueous composition which is obtained by dilution of the liquid concentrate composition should be stable against formation and/or separation of coarse material for at least 12 h.

This object could surprisingly be achieved by a liquid pesticide concentrate composition which comprises a) at least one organic pesticide compound C having a water solubility of not more than 5 g/l, in particular of not more than 1 g/l at 25° C./1013 mbar, b) at least one organic solvent S having a water solubility of at least 10 g/l at 25° C./1013 mbar, and which is capable of dissolving the pesticide compound C, or a mixture of at least one organic solvent S with water, provided that the weight ratio of water to solvent S does not exceed 1:2, c) at least one non-ionic blockcopolymer P comprising at least one polyethyleneoxide moiety PEO and at least one hydrophobic polyether moiety consisting of repeating units selected from $C_3$-$C_{10}$-alkyleneoxides and styrene oxide, d) optionally one ore more non-polymeric surfactants, wherein the weight ratio of the non-ionic blockcopolymer to the organic pesticide compound P:C is from 0.6:1 to 10:1 and wherein the components a), b), c) and optionally d) make up at least 95% of the composition.

The compositions of the invention are stable against formation of solids upon storage and can be easily diluted with water without the formation of coarse material. Moreover, the formulation can be loaded with active ingredients in amounts up to 60% by weight. Surprisingly chemical degradation of some active ingredients having chemically labile groups, such as hydrazones, semicarbazones, urethanes, sulfonyl ureas, amidosulfonylamides, oxime ethers, phosphonic esters, phosphate esters, and the like is decreased in comparison with other solvent based concentrate formulations.

Upon dilution with water, the compositions of the present invention form a bluish or even clear emulsion or dispersion, indicating that the droplets/solids dispersed therein are of very small size, the average particle diameter not exceeding 300 nm, preferably not exceeding 200 nm. The average particle diameter as referred herein, are weight average particle diameters which can be determined by dynamic light scattering. A skilled person is familiar with these methods which are e.g. described in H. Wiese (D. Distler, Ed.), Aqueous Polymer Dispersions (Wässrige Polymerdispersionen), Wiley-VCH 1999, Chapter 4.2.1, p. 40ff, and the literature cited therein; H. Auweter, D. Horn, J. Colloid Interf. Sci. 105 (1985), p. 399; D. Lilge, D. Horn, Colloid Polym. Sci. 269 (1991), p. 704; and H. Wiese, D. Horn, J. Chem. Phys. 94 (1991), p. 6429.

Surprisingly the aqueous compositions, that are obtained by diluting the liquid pesticide compositions with water, have enhanced physical stability, i.e. the formation of solids during dilution and after 24 h after dilution is not observed. Moreover chemical degradation in the diluted compositions of labile active ingredients such as sulfonyl ureas, hydrazones and the like, e.g. by hydrolysis, is decreased.

Surprisingly, the liquid compositions result in an improved biological performance of the active ingredients.

The liquid compositions comprise at least one non-ionic blockcopolymer P, which comprises at least one and preferably at least two polyethyleneoxide moiety PEO and at least one poly-$C_3$-$C_4$-alkyleneoxid moiety PAO.

The non-ionic blockcopolymers usually make up from 10 to 80% by weight, preferably 15 to 50% by weight and in particular 20 to 50% by weight of the non-aqueous composition according to the invention. The weight ratio of non-ionic blockcopolymer P to pesticide compound C is preferably from 0.8:1 to 5:1 more preferably from 0.9:1 to 4:1, and in particular from 1:1 to 3:1.

The PAO moiety in the non-ionic blockcopolymer P usually comprises at least 3, preferably at least 5, in particular 10 to 100 repeating units (number average) which are derived from $C_3$-$C_{10}$ alkyleneoxides, such as propyleneoxide, 1,2-butyleneoxide, cis- or trans-2,3-butyleneoxide or isobutyleneoxide, 1,2-pentenoxide, 1,2-hexene oxide, 1,2-decene oxide or styrene oxide. Thus, the PAO moieties can be described by the general formula $(-O-CHR^x-CHR^y)_q$, wherein q is the number of repeating units in the PAO moiety, $R^x$ and $R^y$ are independently selected from $C_1$-$C_8$ alkyl and hydrogen, provided that at least one of the radicals $R^x$, $R^y$ is different from hydrogen and the total number of carbon atoms of $R^x$ and $R^y$ in one repeating unit is from 1 to 8. One of the radicals $R^x$ or $R^y$ may also be a phenyl radical while the other is hydrogen.

Preferably the repeating units in the PAO moiety are derived from $C_3$-$C_4$ alkyleneoxides. Preferably, the PAO moieties comprise at least 50% by weight and more preferably at least 80% by weight of repeating units derived from propyleneoxide. If the PAO moiety comprises different repeating units, these different repeating units may be arranged statistically or preferably blockwise.

The PEO moieties of the non-ionic blockcopolymer P usually comprise at least 3, preferably at least 5, and more preferably at least 10 repeating units derived from ethyleneoxide (number average). Thus, the PEO moiety can be described by the general formula $(CH_2-CH_2-O)_p$, wherein p is the number of repeating units within the PEO moiety.

The total number of ethyleneoxide repeating units and repeating units in the PAO moiety or moieties will usually be in the range from 20 to 2,000, preferably 40 to 1,000 and in particular 65 to 450 (number average). Among the non-ionic blockcopolymers P those are preferred which have a number average molecular weight $M_N$ ranging from 1,000 to 100,000 Dalton, preferably from 2,000 to 60,000 Dalton, more preferably from 2,500 to 50,000 Dalton and in particular from 3,000 to 20,000 Dalton.

The weight ratio of PEO moieties and PAO moieties (PEO:PAO) in the non-ionic blockcopolymer usually ranges from 1:10 to 10:1, preferably from 1:10 to 2:1, more preferably from 2:8 to 7:3 and in particular from 3:7 to 6:4.

In general, the PEO moieties and the PAO moieties make up at least 80% by weight and preferably at least 90% by weight, e.g. 90 to 99.5% by weight of the non-ionic blockcopolymer P.

Among the blockcopolymers P those are preferred which have a HLB-value ranging from 5 to 20 and in particular from 7 to 18.

Preferred blockcopolymers for use in the compositions of the invention can be described by the following formulae P1 to P5:

$R^1-PEO-O-PAO-R^2$      P1

$R^1-PAO-O-PEO-H$      P2

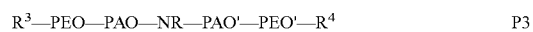

$R^3-PEO-PAO-NR-PAO'-PEO'-R^4$      P3

$R^3-PEO-PAO-(O-A)_n-O-PAO'-PEO'-R^4$      P4

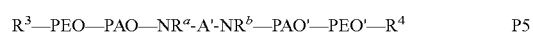

$R^3-PEO-PAO-NR^a-A'-NR^b-PAO'-PEO'-R^4$      P5 wherein n is 0 or 1,

A, A' are a bivalent organic radical which has 2 to 20 carbon atoms and which may carry 1 or 2 hydroxy groups and/or 1, 2, 3 or 4 ether moieties and which may also carry 1 or 2 radicals of the formula $R^2-PEO-PAO-PAO$, PAO' are PAO moieties as defined above, in particular poly-$C_3$-$C_4$-alkylenoxide moieties, PEO, PEO' are polyethyleneoxide moieties, R is $C_1$-$C_{20}$ alkyl or a radical $R^2-PEO-PAO-$ $R^1$ is $C_1$-$C_{20}$ alkyl or $C_1$-$C_{20}$ alkylphenyl, $R^2$, $R^3$, $R^4$ are each independently hydrogen, $C_1$-$C_8$ alkyl, $C_1$-$C_8$ alkylcarbonyl, or benzyl, and $R^a$, $R^b$ are each independently hydrogen, $C_1$-$C_8$ alkyl or a radical $R^2-PEO-PAO-$.

A skilled person will readily understand that the radicals $R^1$, $R^2$, $R^3$ and $R^4$ in formulae P1 to P5 are linked to the PEO or PAO moiety via an oxygen atom.

$R^1$ and $R^2$ in formulae P1 and P2 are preferably $C_1$-$C_{20}$ alkyl and in particular $C_1$-$C_8$ alkyl, such as methyl, ethyl, n-propyl, isopropyl, n-butyl, 2-butyl, n-pentyl, n-hexyl, n-heptyl, n-octyl, 2-ethylhexyl, n-decyl, isodecyl, 3-propylhexyl and the like. $R^2$ in formula P1 is preferably hydrogen. $R^3$ and $R^4$ in formulae P3, P4 and P5 are preferably hydrogen. R in formula P3 is preferably $C_1$-$C_{20}$ alkyl, in particular $C_4$-$C_{20}$ alkyl.

Suitable radicals A and A' in formulae P4 and P5 may be aliphatic or cycloaliphatic radicals or aromatic radicals or mixed aromatic/aliphatic or mixed aliphatic/cycloaliphatic radicals. Examples for aliphatic radicals A and A' are $C_2$-$C_{20}$ alkandiyl, wherein 1, 2, 3 or 4 $CH_2$-moieties may be replaced by oxygen or sulfur, e.g. ethane-1,2-diyl, propane-1,3-diyl, butane-1,4-diyl, hexane-1,4-diyl, 3-oxapentane-1,5-diyl, 3-oxahexane-1,6-diyl, 4-oxaheptane-1,7-diyl, 3,6-dioxaoctane-1,8-diyl, 3,7-dioxanonane-1,9-diyl and 3,6,9-trioxaundecan-1,11-diyl. Examples of cycloaliphatic radicals A, A' comprise $C_5$-$C_8$-cycloalkane-diyl and $C_7$-$C_{12}$ bicycloalkanediyl, which may carry 1, 2, 3 or 4 $C_1$-$C_4$-alkyl groups, e.g. methyl groups, such as cyclohexane-1,2-, -1,3-, and -1,4-diyl. Aromatic radicals A, A' are for example 1,2-phenylene, 1,3-phenylene, 1,4-phenylene. Mixed aliphatic/aromatic radicals A, A' are those which comprise one or more alkanediyl units and at least one aromatic unit such as a phenyl ring. Examples for mixed aliphatic/aromatic radicals A, A' comprise diphenylmethane-4,4'-diyl, 4,4'-[2,2-bis(phenyl)propane]diyl and the like. Mixed aliphatic/cycloaliphatic radicals A, A' are those which comprise one or more alkanediyl units and at least one cycloaliphatic unit such as a cyclohexane ring. Examples for mixed aliphatic/cycloaliphatic radicals A, A' comprise methylcyclohexane-1,7-diyl, 4,4'-[bis(cyclohexyl)methane]diyl, 4,4'-[2,2-bis(cyclohexyl)propane]diyl and the like. Preferred radicals A, A' are selected from $C_2$-$C_{20}$ alkandiyl, wherein 1, 2, 3 or 4 $CH_2$-moieties may be replaced by oxygen.

Amongst the non-ionic blockcopolymers of formulae P1 to P5 those of formulae P2 and P4 are especially preferred.

According to the invention, a single type of non-ionic blockcopolymer P or different types of blockcopolymers P may be used. In a preferred embodiment the non-aqueous liquid pesticide composition comprises at least 2, e.g. 2, 3 or 4 different types of non-ionic blockcopolymers P. Different types means that the blockcopolymers are distinct with regard to at least one of the following features: molecular weight, weight ratio of PEO to PAO, the HLB-value or the molecular architecture. Preferably at least one of the blockcopolymers combines at least two of the preferred features. In such mixtures the blockcopolymer P that combines at least two of the preferred features makes up at least 20% by weight, preferably at least 30% by weight, e.g. 20 to 90% by weight, in particular 30 to 80% by weight of the total amount of blockcopolymer P in the composition.

Non-ionic blockcopolymers P are known in the art and commercially available under the trade names Pluronic®, such as Pluronic® P 65, P84, P 103, P 105, P 123 and Pluronic® L 31, L 43, L 62, L 62 LF, L 64, L 81, L 92 and L 121, Pluraflo® such as Pluraflo® L 860, L1030 and L 1060Tetronic®, such as Tetronic® 704, 709, 1104, 1304, 702, 1102, 1302, 701, 901, 1101, 1301 (BASF Aktiengesellschaft), Agrilan® AEC 167 and Agrilan® AEC 178 (Akcros Chemicals), Antarox® B/848 (Rhodia), Berol® 370 and Berol® 374 (Akzo Nobel Surface Chemistry), Dowfax® 50 C15, 63 N10, 63 N30, 64 N40 and 81 N10 (Dow Europe), Genapol® PF (Clariant), Monolan®, such as Monolan® PB, Monolan® PC, Monolan® PK (Akcros Chemicals), Panox® PE (Pan Asian Chemical Corporation), Symperonic®, such as Symperonic® PE/L, Symperonic® PE/F, Symperonic® PE/P, Symperonic® PE/T (ICI Surfactants), Tergitol® XD, Tergitol® XH and Tergitol® XJ (Union Carbide), Triton® CF-32 (Union Carbide), Teric PE Series (Huntsman) and Witconol®, such as Witconol® APEB, Witconol® NS 500 K and the like.

The non-aqueous liquid pesticide composition usually contains at least one, e.g. 1, 2, 3 or 4 organic solvents S which have a water-solubility of at least 10 g/, preferably at least 50 g/l, in particular at least 100 g/l at 25° C./1013 mbar. In a preferred embodiment the solvent S is completely miscible with water. The solvent S should be capable of dissolving the pesticide compound C, i.e. the solubility of the pesticide compound C in the mixture of the at least one organic solvent S and the non-ionic blockcopolymer P should be sufficient to achieve a complete dissolution of the organic pesticide compound C contained in the non-aqueous liquid pesticide composition of the invention. It is evident that the type of organic solvent S will depend on the organic pesticide compound C to be formulated in the non-aqueous liquid pesticide composition. However, the skilled person can easily select an appropriate solvent by routine experiments.

The liquid compositions of the invention may also comprise a mixture of at least one organic solvent S with water, provided that the weight ratio of water to solvent S does not exceed 1:2 and in particular 1:3 is equal or below, e.g. 1:3 to 1:100 or from 1:5 to 1:50. In another embodiment, the compositions do not contain water, i.e. the weight ratio of solvent to water is below 1:50, in particular below 1:100. In this case, the solvent S is preferably completely miscible with water. Preferably, the amount of water does not exceed 20% by weight, in particular 10% by weight of the liquid pesticide concentrate. If water is present, the amount is preferably from 0.1 to 20% by weight, in particular from 0.2 to 10% by weight of the liquid pesticide concentrate.

In general, suitable organic solvents are:

$C_1$-$C_8$ alkanols and $C_5$-$C_8$ cycloalkanols, such as methanol, ethanol, n-propanol, isopropanol, n-butanol, isobutanol, 2-butanol, tert.-butanol, pentanol, isoamyl alcohol, n-hexanol, 1-methylpentanol, 1-ethylbutanol, n-octanol, 2-ethylhexanol, cyclopentanol, cyclohexanol and the like;

polyhydric alcohols, such as ethylene glycol, 1,2-propanediol, 1,3-propanediol, 1,4-butanediol, neopentyl glycol, pinacol, pentanediols, hexane diols, glycerol, sorbitol and the like;

alkylene glycol monomethyl ethers, monoethyl ethers and dimethyl ethers, such as ethylene glycol monomethyl ether, ethylene glycol dimethyl ether, propylene glycol monomethyl ether, ethylene glycol monoethyl ether, and technical mixtures such as Carbitols, Cellosolves, Dowanols, Jefferols, Ektasolves, and the like;

cyclic ethers which may contain an OH group such as tetrahydrofuran, pyran, dioxan, tetrahydrofurfurol;

di- and tri-$C_2$-$C_4$-alkylene glycols and their monomethyl, monoethyl- and dimethyl ethers, such as diethylene glycol monomethyl ether, diethylene glycol dimethyl ether, dipropylene glycol and dipropylene glycol monomethyl ether;

ketones, having from 3 to 8 C-atoms and optionally a hydroxyl group, such as acetone, methylethyl ketone, methylpropyl ketone, methyl-4-hydroxybutyl ketone, cyclopentanone, cyclohexanone, diaceton alcohol, mesityloxide;

lactones, having from 3 to 8 C-atoms, such as β-propiolactone, γ-butyrolactone, carbonates, in particular dimethylcarbonat, diethylcarbonat and 2-Oxa-1,3-dioxolan (ethylene carbonate) and 2-oxa-1,3-dioxan (propylene carbonate);

organic acids having from 1 to 8 carbon atoms, preferably 1 to 3 carbon atoms, such as acetic acid, propionic acid, butyric acid, hexanoic acid, caprylic acid;

amines, in particular alkylamines, dialkylamines and trialkylamines having from 1 to 8 carbon atoms, preferably from 2 to 6 carbon atoms, such as methylamine, ethylamine, diisopropylamine, n-butylamine, isobutylamine, n-pentylamine, isopentylamine, di-n-propylamine, isopropylamine, as well as heterocyclic amines, such as piperidine, piperazine, morpholine and pyrrolidine, amides, n-$C_1$-$C_8$-alkylamides and N,N—$C_1$-$C_2$-dialkylamides of $C_1$-$C_4$-aliphatic acids in particular of formic acid or acetic acid, such as formamide, acetamide, dimethylformamide, dimethylacetamid, $C_2$-$C_4$-alkanolamines, $C_2$-$C_4$-dialkanolamines and $C_2$-$C_4$-trialkanolamines, such as monoethanolamine, diethanolamine, triethanolamine, 2-methylaminoethanol, 2-dimethylaminoethanol, isopropanolamine, diisopropanolamine and the like;

$C_1$-$C_4$-alkylesters of formic acid or acetic acid such as methyl formate, ethyl formate, methyl acetate, ethyl acetate, n-propyl acetate isopropyl acetate and the like;

heterocyclic aromatic or aliphatic amines having preferably from 2 to 6 carbon atoms, 1 or 2 nitrogen atoms and optionally 1 or 2 further heteroatoms selected from O and S, such as pyrrole, pyridine, picoline, morpholine, piperidine, piperazine, heterocyclic aldehydes such as furfural; and lactames, having preferably from 3 to 6 carbon atoms and their N-methyl and N-ethyl derivatives, such as pyrrolidin-2-one, N-methylpyrrolidin-2-one, N-ethylpyrrolidin-2-one, etc.

The amount of solvent S in the non-aqueous pesticide composition of the invention usually ranges from 10 to 80% by weight, preferably from 20 to 70% by weight and in particular 30 to 60% by weight. In case the liquid pesticide composition contains water the total amount of solvent S+water preferably ranges from 20 to 70% by weight and in particular 30 to 60% by weight The compositions of the invention also comprise at least one organic pesticide compound C which is sparingly soluble or insoluble in water. Preferably the solubility is below 0.5 g/l and in particular below 0.1 g/l at 25° C. and 1013 mbar.

The pesticide compound C can be selected from each group of active ingredients which are used to protect plants/crops from attack or infestation by harmful organisms, i.e. the pesticide compound can be selected from acaricides, algicides, antecedents, aricides, bactericides, bird repellents, chemosterilans, fungicides, herbicides, herbicide safeners, insect attractants, insect repellents, insecticides, mammal repellents, mating disrupters, moluscicides, nematicides, plant activators, plant growth regulators, rhodenticides, synergists, virucides and other compounds with exert an action on the plants to be protected and/or against the harmful organism.

Examples of suitable pesticide compounds C which act as fungicides are for example:

acylalanine, such as benalaxyl, metalaxyl, ofurace, oxadixyl;

amine derivatives, such as aldimorph, dodine, dodemorph, fenpropimorph, fenpropidin, guazatine, iminoctadine, spiroxamin, tridemorph;

anilinopyrimidine, such as pyrimethanil, mepanipyrim or cyrodinyl;

antibiotics, such as cycloheximid, griseofulvin, kasugamycin, natamycin, polyoxin und streptomycin;

azoles, such as bitertanol, bromoconazol, cyproconazole, difenoconazol, dinitroconazol, epoxiconazol, fenbuconazol, fluquiconazol, flusilazol, flutriafol, hexaconazol, imazalil, ipconazol, metconazol, myclobutanil, penconazol, propiconazol, prochloraz, prothioconazol, tebuconazol, tetraconazol, triadimefon, triadimenol, triflumizol, triticonazol;

2-methoxybenzophenones, e.g. those disclosed in EP-A 897 904 by the general formula I, e.g. metrafenon;

dichlorophenyl dicarboximides, such as chlozolinate, dichlozoline, isovaledione, iprodion, myclozolin, procymidon, vinclozolin;

dithiocarbamates, such as ferbam, nabam, maneb, mancozeb, metam, metiram, propineb, polycarbamat, thiram, ziram, zineb;

heterocyclic compounds, such as anilazine, benomyl, boscalid, carbendazim, carboxin, oxycarboxin, cyazofamid, dazomet, dithianon, famoxadon, fenamidon, fenarimol, fuberidazoles, flutolanil, furametpyr, isoprothiolanes, mepronil, nuarimol, picobezamid, probenazoles, proquinazid, pyrifenox, pyroquilon, quinoxyfen, silthiofam; thiabendazole, thifluzamid, thiophanat-methyl, tiadinil, tricyclazoles, triforine;

nitrophenyl derivatives, such as binapacryl, dinocap, dinobuton, nitrophthal-isopropyl;

phenylpyrroles, such as fenpiclonil and fludioxonil;

non-classified fungicides, such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetat, fenoxanil, ferimzones, fluazinam, fosetyl, fosetyl-aluminum, iprovalicarb, hexachlorobenzol, metrafenon, pencycuron, propamocarb, phthalides, toloclofos-methyl, quintozenes, zoxamid;

strobilurines, e.g. the compounds disclosed in WO 03/075663 by the general formula I, such as azoxystrobin, dimoxystrobin, fluoxastrobin, kresoxim-methyl, metominostrobin, orysastrobin, picoxystrobin, pyraclostrobin and trifloxystrobin;

sulfenic acid derivatives, such as captafol, captan, dichlofluanid, folpet, tolylfluanid;

cinnamic acid amides and analoga, such as dimethomorph, flumetover, flumorp;

6-aryl-[1,2,4]triazolo[1,5-a]pyrimidines, e.g. those disclosed in WO 98/46608, WO 99,41255 or WO 03/004465 by the general formula I;

amido fungicides, such as cyclofenamid and (Z)—N-[α-(cyclopropylmethoxyimino)-2,3-difluoro-6-(difluoromethoxy)benzyl]-2-phenylacetamid.

Examples of pesticides compounds C which act as herbicides or herbicide safeners comprise 1,3,4-thiadiazoles, such as buthidazoles und cyprazoles;

amides, such as allidochlor, benzoylpropethyl, bromobutide, chlorthiamid, dimepiperate, dimethenamid, diphenamid, etobenzanid, flampropmethyl, fosamin, isoxaben, metazachlor, monalide, naptalame, pronamid, propanil;

aminophosphoric acids, such as bilanafos, buminafos, glufosinateammonium, glyphosates, sulfosates;

aminotriazoles, such as amitrol, anilide, anilofos, mefenacet;

aryloxyalkanoic acids, such as 2,4-D, 2,4-DB, clomeprop, dichlorprop, dichlorprop-P, dichlorprop-P, fenoprop, fluroxypyr, MCPA, MCPB, mecoprop, mecoprop-P, napropamides, napro-panilides, triclopyr, and the $C_1$-$C_8$-alkyl esters, e.g. the ethyl or butyl esters, the $C_1$-$C_4$-alkoxy-$C_1$-$C_4$-alkyl esters, e.g. the 2-ethoxyethyl esters or 2-butoxyethyl esters, and the mono-, di- and tri-$C_1$-$C_8$-alkyl ammonium salts, in particular the triethyl ammonium salts of aryloxyalkanoic acids;

benzoic acids, such as chloramben, dicamba and the $C_1$-$C_8$-alkyl esters, e.g. the ethyl or butyl esters, the $C_1$-$C_4$-alkoxy-$C_1$-$C_4$-alkyl esters, e.g. the 2-ethoxyethyl esters or 2-butoxyethyl esters, and the mono-, di- and tri-$C_1$-$C_8$-alkyl ammonium salts, in particular the triethyl ammonium salts of benzoic acids;

benzothiadiazinones, such as bentazon;

bleachers, such as clomazone, diflufenican, fluorochloridones, flupoxam, fluridone, pyrazolates, sulcotrione;

carbamates, such as carbetamid, chlorbufam, chlorpropham, desmedipham, phenmedipham, vernolate;

quinolinic acids, such as quinclorac, quinmerac;

dichloropropionic acids, such as dalapon;
dihydrobenzofuranes, such as ethofumesates;
dihydrofuran-3-ones, such as flurtamone;
dinitroanilines, such as benefin, butralin, dinitramin, ethalfluralin, fluchloralin, isopropalin, nitralin, oryzalin, pendimethalin, prodiamines, profluralin, trifluralin, dinitrophenoles, such as bromofenoxim, dinoseb, dinoseb-acetate, dinoterb, DNOC, minoterb-acetate;
diphenylether, such as acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen, oxyfluorfen;
imidazoles, such as isocarbamid;
imidazolinones, such as imazamethapyr, imazapyr, imazaquin, imazethabenzmethyl, imazethapyr, imazapic, imazamox;
oxadiazoles, such as methazole, oxadiargyl, oxadiazon;
oxiranes, such as tridiphane;
phenoles, such as bromoxynil, ioxynil;
phenoxyphenoxypropionic acid esters, such as clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxy-ethyl, haloxyfop-methyl, haloxyfop-p-methyl, isoxapyrifop, propaquizafop, quizalofop-ethyl, quizalofop-p-ethyl, quizalofop-tefuryl;
phenylacetic acids and their esters, such as chlorfenac;
phenylpropionic acids and their esters, such as chlorophenprop-methyl;
ppi-active ingredients, such as benzofenap, flumiclorac-pentyl, flumioxazin, flumipropyn, flupropacil, pyrazoxyfen, sulfentrazone, thidiazimin;
pyrazoles, such as nipyraclofen;
pyridazines, such as chloridazon, maleic hydrazide, norflurazon, pyridate;
pyridincarbonic acids, such as clopyralid, dithiopyr, picloram, thiazopyr;
pyrimidylethers, such as pyrithiobac acid, pyrithiobac-sodium, KIH-2023, KIH-6127;
sulfonamides, such as flumetsulam, metosulam;
triazolcarboxamides, such as triazofenamid;
uraciles, such as bromacil, lenacil, terbacil;
further benazolin, benfuresate, bensulide, benzofluor, bentazon, butamifos, cafenstroles, chlorthal-dimethyl, cinmethylin, dichlobenil, endothall, fluorbentranil, mefluidide, perfluidones, piperophos, topramezone and prohexandion-calcium;
urea herbicides, such as benzthiazuron, cumyluron, cycluron, dichloralylurea, diflufenzopyr, isononuron, isouron, methabenzthiazuron, monisuron, noruron;
phenylurea herbicides, such as anisuron, buturon, chlorbromuron, chlorturon, chlorotoluron, choroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluoron;
sulfonyl ureas, such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuronethyl, rimsulfuron, sulfometuron-methyl, thifensulfuron-methyl, triasulfuron, tribenuron-methyl, triflusulfuron-methyl, tritosulfuron;
plant protection active ingredients, type cyclohexanone, such as alloxydim, clethodim, cloproxydim, cycloxydim, sethoxydim and tralkoxydim. Most preferred herbicidal active ingredients type cyclohexenone are: tepraloxydim (see AGROW, no. 243, Mar. 11, 1995, page 21, caloxydim) and 2-(1-[2-{4-Chlorphenoxy}propyl-oxyimino]butyl)-3-hydroxy-5-(2H-tetrahydro-thiopyran-3-yl)-2-cyclohexen-1-on and type sulfonyl urea: N-(((4-methoxy-6-[trifluormethyl]-1,3,5-triazin-2-yl)amino)carbonyl)-2-(trifluormethyl)-benzolsulfonamid.

Examples for pesticide compounds C which are useful as insecticides, acaricides, nematicides and/or miticides comprise:

organophosphates, such as acephates, azinphos-methyl, chlorpyrifos, chlorfenvinphos, diazinon, dichlorvos, dimethylvinphos, dioxabenzofos, dicrotophos, dimethoate, disulfoton, ethion, EPN, fenitrothion, fenthion, isoxathion, malathion, methamidophos, methidathion, methyl-parathion, mevinphos, monocrotophos, oxydemeton-methyl, paraoxon, parathion, phenthoates, phosalones, phosmet, phosphamidon, phorates, phoxim, pirimiphos-methyl, profenofos, prothiofos, primiphos-ethyl, pyraclofos, pyridaphenthion, sulprophos, triazophos, trichlorfon; tetrachlorvinphos, vamidothion;

carbamates, such as alanycarb, benfuracarb, bendiocarb, carbaryl, carbofuran, carbosulfan, fenoxycarb, furathiocarb, indoxacarb, methiocarb, methomyl, oxamyl, pirimicarb, propoxur, thiodicarb, triazamate;

pyrethroides, such as bifenthrin, cyfluthrin, cycloprothrin, cypermethrin, deltamethrin, esfenvalerate, ethofenprox, fenpropathrin, fenvalerate, cyhalothrin, lambda-cyhalothrin, permethrin, silafluofen, tau-fluvalinate, tefluthrin, tralomethrin, alpha-cypermethrin, zeta-cypermethrin, permethrin;

arthropodic growth regulators: a) chitinsynthesis inhibitors, e.g. benzoyl ureas, such as chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists, such as halofenozide, methoxyfenozide, tebufenozide; c) juvenoides, such as pyriproxyfen, methoprenes, fenoxycarb; d) lipid biosynthesis inhibitors, such as spirodiclofen;

neonicotinoides, such as flonicamid, clothianidin, dinotefuran, imidacloprid, thiamethoxam, nitenpyram, nithiazin, acetamiprid, thiacloprid;

further non-classified insecticids are abamectin, acequinocyl, acetamiprid, amitraz, azadirachtin, bensultap, bifenazate, cartap, chlorfenapyr, chlordimeform, cyromazines, diafenthiuron, dinetofuran, diofenolan, emamectin, endosulfan, ethiprole, fenazaquin, fipronil, formetanate, formetanate hydrochlorid, gamma-HCH, hydramethylnon, imidacloprid, indoxacarb, isoprocarb, metolcarb, pyridaben, pymetrozine, spinosad, tebufenpyrad, thiamethoxam, thiocyclam, nitenpyram, piperonylbutoxid, thiacloprid, pyridalyl, flonicamid, fluacypyrim, milbemectin, spiromesifen, spirodiclofen, flupyrazofos, NC 512, tolfenpyrad, flubendiamide, fistrifluron, benclothiaz, pyrafluprole, pyriprole, amidoflumet, flufenerim, cyflumetofen, acequinocyl, lepimectin, profluthrin, dimefluthrin, XMC and xylylcarb, N-phenylsemicarbazones as described in EP-A 462 456 by the general formula I, in particular compounds of the general formula A

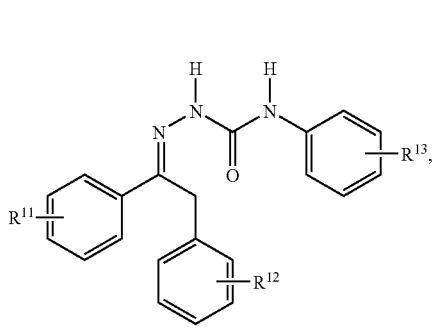

wherein $R^{11}$ and $R^{12}$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^{13}$ is $C_1$-$C_4$ alkoxy, $C_1$-$C_4$ haloalkyl or $C_1$-$C_4$ haloalkoxy, e.g. the compound IV, wherein $R^{11}$ is 3-$CF_3$ and $R^{12}$ is 4-CN and $R^{13}$ is 4-$OCF_3$ (Metaflumizone);

amidrazone compounds of the general formula B

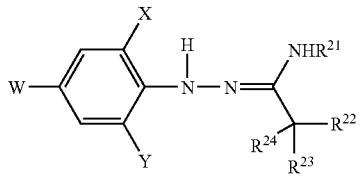

wherein

W is chlorine or trifluoromethyl;

X and Y are each independently chlorine or bromine;

$R^{21}$ is $C_1$-$C_6$-alkyl, $C_3$-$C_6$-alkenyl, $C_3$-$C_6$-alkynyl, or $C_3$-$C_6$-cycloalkyl which may be substituted with 1 to 3 halogen atoms, or $C_2$-$C_4$-alkyl which is substituted by $C_1$-$C_4$-alkoxy;

$R^{22}$ and $R^{23}$ are $C_1$-$C_6$-alkyl or may together with the carbon atom, to which they are bound, form $C_3$-$C_6$-cycloalkyl which may be unsubstituted or substituted by 1 to 3 halogen atoms;

$R^{24}$ is hydrogen or $C_1$-$C_6$-alkyl, including the enantiomers and salts thereof.

In formula B, $R^{21}$ is preferably $C_1$-$C_4$-alkyl, in particular methyl or ethyl. In formula B, $R^{22}$ and $R^{23}$ are preferably $C_1$-$C_4$-alkyl, in particular methyl, or $R^{22}$ and $R^{23}$ together with the carbon atom to which they are bound form a cyclopropyl ring, which may carry 1 or 2 chlorine atoms. $R^{24}$ is preferably $C_1$-$C_4$-alkyl, in particular methyl. W is preferably trifluoromethyl. X and Y are preferably chlorine. Preferred examples are compounds of the formula B, wherein X and Y are chlorine, W is trifluoromethyl, $R^{22}$, $R^{23}$ and $R^{24}$ are methyl and $R^{21}$ is methyl or ethyl as well as compounds of the formula B, wherein X and Y are chlorine, W is trifluoromethyl, $R^{22}$ and $R^{23}$ together with the carbon atom to which they are bound form a 2,2-dichlorocyclopropyl ring $R^{24}$ is methyl and $R^{21}$ is methyl or ethyl.

compounds of the following formula as described in WO 98/05638

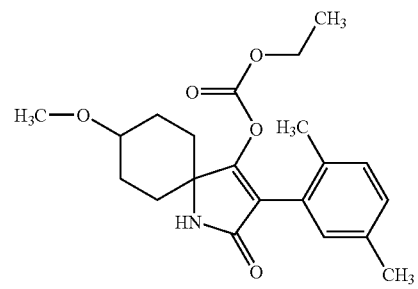

Aminoisothiazoles of the formula

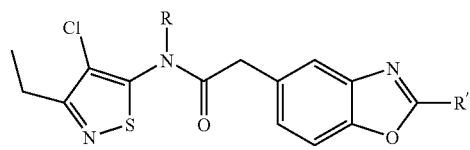

wherein
R=—$CH_2$O $CH_3$ or H and
R'=—$CF_2CF_2CF_3$;

Anthranilamides of the formula

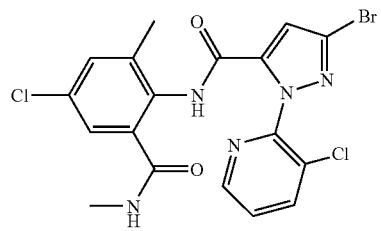 [SMILES: CNC(=O)c1cc(Cl)cc(C)c1NC(=O)c1cc(Br)nn1-c1ncccc1Cl]

and compounds of the formulae

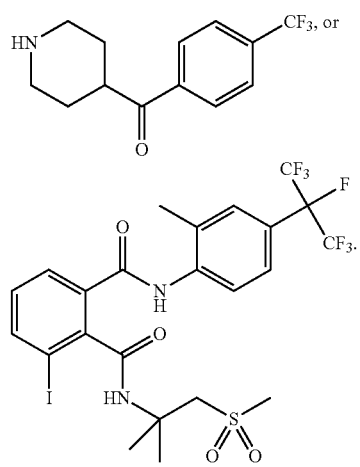

Examples of plant growth regulators comprise gibberellines and oximes, such as {[(isopropylidene)amino]oxy}acetic acid-2-methoxy-2-oxoethyl ester, and also defoliants, such as thidiazuron, growth inhibitors, such as butralin, flumetralin, fluoridamid, prohydrojasmon, growth retardants, such as paclobutrazol, uniconazole, growth stimulators, such as brassinolide, forchlorfenuron and the like.

The compositions of the present invention are particularly useful for formulating pesticide compound C, which are selected from fungicides, insecticides, acaricides, nematicides and herbicides.

In a preferred embodiment of the compositions of the present invention the pesticide compound C comprises at least one insecticide compound.

A particularly preferred embodiment relates to pesticide compositions which comprise a compound of formula A as the at least one organic pesticide compound C.

A further particularly preferred embodiment relates to pesticide compositions which comprise a compound of formula B as the at least one organic pesticide compound C. In another preferred embodiment of the compositions of the present invention the pesticide compound C comprises at least one fungicide compound.

Another particularly preferred embodiment of the invention relates to a pesticide composition which comprises at least one fungicide which is selected from strobilurines, such as azoxystrobin, dimoxystrobin, fluoxastrobin, kresoximmethyl, metominostrobin, orysastrobin, picoxystrobin, pyraclostrobin or trifloxystrobin, azol fungicides, in particular conazoles such as epoxyconazole, tebuconazole, triticonazole, fluquinconazole, flutriafol, metconazole, myclobutanil, cycproconazole, prothioconazole and propiconazole, boscalid, dichlorophenyl dicarboximides such as vinclozoline and 6-aryl-[1,2,4]triazolo[1,5-a]pyrimidines, e.g. those disclosed in WO 98/46608, WO 99/41255 and WO 03/004465, in particular compounds of the general formula C

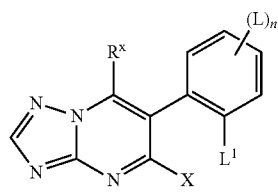

(C)

wherein:
$R^x$ is a group $NR^{14}R^{15}$ or linear or branched $C_1$-$C_8$ alkyl, which may be unsubstituted or substituted by halogen, OH, $C_1$-$C_4$ alkoxy, phenyl or $C_3$-$C_6$ cycloalkyl, $C_2$-$C_6$ alkenyl, $C_3$-$C_6$ cycloalkyl, $C_3$-$C_6$ cycloalkenyl, phenyl or naphthyl, wherein the 4 last-mentioned radicals may be unsubstituted or substituted by 1, 2, 3 or 4 radicals, selected from halogen, OH, $C_1$-$C_4$ alkyl, $C_1$-$C_4$ halogenalkoxy, $C_1$-$C_4$ alkoxy and $C_1$-$C_4$ halogenalkyl;
$R^{14}$, $R^{15}$ are each independently hydrogen, $C_1$-$C_8$ alkyl, $C_1$-$C_8$ halogenalkyl, $C_3$-$C_{10}$ cycloalkyl, $C_3$-$C_6$ halogencycloalkyl, $C_2$-$C_8$ alkenyl, $C_4$-$C_{10}$ alkadienyl, $C_2$-$C_8$ halogenalkenyl, $C_3$-$C_6$ cycloalkenyl, $C_2$-$C_8$ halogencycloalkenyl, $C_2$-$C_8$ alkinyl, $C_2$-$C_8$ halogenalkinyl or $C_3$-$C_6$ cycloalkinyl,
$R^{14}$ and $R^{15}$ together with the nitrogen atom to which they are bound may also form a 5-, 6-, 7- or 8-membered heterocycle which may contain 1, 2 or 3 additional heteroatoms selected from N, O and S, and which may carry one or more (e.g. 1, 2 or 3) radicals selected from the group consisting of halogen, $C_1$-$C_6$ alkyl, $C_1$-$C_6$ halogenalkyl, $C_2$-$C_6$ alkenyl, $C_2$-$C_6$ halogenalkenyl, $C_1$-$C_6$ alkoxy, $C_1$-$C_6$ halogenalkoxy, $C_3$-$C_6$ alkenyloxy, $C_3$-$C_6$ halogenalkenyloxy, (exo)-$C_1$-$C_6$-alkylen and oxy-$C_1$-$C_3$-alkylenoxy;
L is selected from halogen, cyano, $C_1$-$C_6$ alkyl, $C_1$-$C_4$ halogenalkyl, $C_1$-$C_6$ alkoxy, $C_1$-$C_4$ halogenalkoxy and $C_1$-$C_6$ alkoxycarbonyl;
$L^1$ is halogen, $C_1$-$C_6$ alkyl or $C_1$-$C_6$ halogenalkyl and in particular fluorine or chloro;
X is halogen, $C_1$-$C_4$ alkyl, cyano, $C_1$-$C_4$ alkoxy or $C_1$-$C_4$ halogenalkyl and preferably halogen or methyl.

Examples for compounds C are:
5-chloro-7-(4-methylpiperidin-1-yl)-6-(2,4,6-trifluorophenyl)-[1,2,4]triazolo[1,5-a]-pyrimidine,
5-chloro-7-(4-methylpiperazin-1-yl)-6-(2,4,6-trifluorophenyl)-[1,2,4]triazolo[1,5-a]-pyrimidine,
5-chloro-7-(morpholin-1-yl)-6-(2,4,6-trifluorophenyl)-[1,2,4]triazolo[1,5-a]pyrimidine,
5-chloro-7-(piperidin-1-yl)-6-(2,4,6-trifluorophenyl)-[1,2,4]triazolo[1,5-a]pyrimidine,
5-chloro-7-(morpholin-1-yl)-6-(2,4,6-trifluorophenyl)-[1,2,4]triazolo[1,5-a]pyrimidine,
5-chloro-7-(isopropylamino)-6-(2,4,6-trifluorohenyl)-[1,2,4]triazolo[1,5-a]pyrimidine,
5-chloro-7-(cyclopentylamino)-6-(2,4,6-trifluorohenyl)-[1,2,4]triazolo[1,5-a]pyrimidine
5-chloro-7-(2,2,2-trifluorethylamino)-6-(2,4,6-trifluorophenyl)-[1,2,4]triazolo[1,5-a]-pyrimidine,
5-chloro-7-(1,1,1-trifluoropropan-2-ylamino)-6-(2,4,6-trifluorophenyl)-[1,2,4]triazolo[1,5-a]pyrimidine,
5-chloro-7-(3,3-dimethylbutan-2-ylamino)-6-(2,4,6-trifluorophenyl)-[1,2,4]triazolo[1,5-a]pyrimidine,
5-chloro-7-(cyclohexylmethyl)-6-(2,4,6-trifluorophenyl)-[1,2,4]triazolo[1,5-a]pyrimidine,
5-chloro-7-(cyclohexyl)-6-(2,4,6-trifluorophenyl)-[1,2,4]triazolo[1,5-a]pyrimidine,
5-chloro-7-(2-methylbutan-3-yl)-6-(2,4,6-trifluorophenyl)-[1,2,4]triazolo[1,5-a]pyrimidine,
5-chloro-7-(3-methylpropan-1-yl)-6-(2,4,6-trifluorophenyl)-[1,2,4]triazolo[1,5-a]-pyrimidine,
5-chloro-7-(4-methylcyclohexan-1-yl)-6-(2,4,6-trifluorophenyl)-[1,2,4]triazolo[1,5-a]pyrimidine,
5-chloro-7-(hexan-3-yl)-6-(2,4,6-trifluorophenyl)-[1,2,4]triazolo[1,5-a]pyrimidine,
5-chloro-7-(2-methylbutan-1-yl)-6-(2,4,6-trifluorophenyl)-[1,2,4]triazolo[1,5-a]pyrimidine,
5-chloro-7-(3-methylbutan-1-yl)-6-(2,4,6-trifluorophenyl)-[1,2,4]triazolo[1,5-a]pyrimidine,
5-chloro-7-(1-methylpropan-1-yl)-6-(2,4,6-trifluorophenyl)-[1,2,4]triazolo[1,5-a]-pyrimidine,
5-methyl-7-(4-methylpiperidin-1-yl)-6-(2,4,6-trifluorophenyl)-[1,2,4]triazolo[1,5-a]-pyrimidine,
5-methyl-7-(4-methylpiperazin-1-yl)-6-(2,4,6-trifluorophenyl)-[1,2,4]triazolo[1,5-a]-pyrimidine,
5-methyl-7-(morpholin-1-yl)-6-(2,4,6-trifluorophenyl)-[1,2,4]triazolo[1,5-a]pyrimidine,
5-methyl-7-(piperidin-1-yl)-6-(2,4,6-trifluorophenyl)-[1,2,4]triazolo[1,5-a]pyrimidine,
5-methyl-7-(morpholin-1-yl)-6-(2,4,6-trifluorophenyl)-[1,2,4]triazolo[1,5-a]pyrimidine,
5-methyl-7-(isopropylamino)-6-(2,4,6-trifluorophenyl)-[1,2,4]triazolo[1,5-a]pyrimidine,
5-methyl-7-(cyclopentylamino)-6-(2,4,6-trifluorophenyl)-[1,2,4]triazolo[1,5-a]pyrimidine,
5-methyl-7-(2,2,2-trifluoroethylamino)-6-(2,4,6-trifluorophenyl)-[1,2,4]triazolo[1,5-a]-pyrimidine,
5-methyl-7-(1,1,1-trifluoropropan-2-ylamino)-6-(2,4,6-trifluorophenyl)-[1,2,4]triazolo[1,5-a]pyrimidine, 5-methyl-7-(3,3-dimethylbutan-2-ylamino)-6-(2,4,6-trifluorophenyl)-[1,2,4]triazolo[1,5-a]-pyrimidine,
5-methyl-7-(cyclohexylmethyl)-6-(2,4,6-trifluorophenyl)-[1,2,4]triazolo[1,5-a]pyrimidine,
5-methyl-7-(cyclohexyl)-6-(2,4,6-trifluorophenyl)-[1,2,4]triazolo[1,5-a]pyrimidine,
5-methyl-7-(2-methylbutan-3-yl)-6-(2,4,6-trifluorophenyl)-[1,2,4]triazolo[1,5-a]-pyrimidine,
5-methyl-7-(3-methylpropan-1-yl)-6-(2,4,6-trifluorophenyl)-[1,2,4]triazolo[1,5-a]-pyrimidine,
5-methyl-7-(4-methylcyclohexan-1-yl)-6-(2,4,6-trifluorophenyl)-[1,2,4]triazolo[1,5-a]-pyrimidine,
5-methyl-7-(hexan-3-yl)-6-(2,4,6-trifluorophenyl)-[1,2,4]triazolo[1,5-a]pyrimidine,
5-methyl-7-(2-methylbutan-1-yl)-6-(2,4,6-trifluorophenyl)-[1,2,4]triazolo[1,5-a]-pyrimidine,
5-methyl-7-(3-methylbutan-1-yl)-6-(2,4,6-trifluorophenyl)-[1,2,4]triazolo[1,5-a]pyrimidine and
5-methyl-7-(1-methylpropan-1-yl)-6-(2,4,6-trifluorophenyl)-[1,2,4]triazolo[1,5-a]-pyrimidine.

The amount of active ingredient in the liquid compositions is usually at least 1% by weight, preferably at least 5% by weight, particularly at least 8% by weight and more preferably at least 10% by weight. The amount of active ingredient will in general not exceed 60% by weight and is preferably up to 50% by weight and in particular up to 40% by weight, based on the total weight of the composition.

The liquid compositions of the invention may also comprise a non-polymeric surfactant (component d). This additional surfactant serves to further stabilize the active ingredient particles in the aqueous composition which is obtained upon dilution of the liquid composition according to the invention. In a preferred embodiment of the invention, the liquid composition comprises the at least one non-polymeric surfactant in an amount from 0.1 to 10% by weight, preferably from 0.5 to 5% by weight, based on the total weight of the composition.

In another preferred embodiment of the invention, the liquid composition contains no or less than 0.1% by weight, based on the total weight of the composition, of a non-polymeric surfactant.

In contrast to the blockcopolymers P, the non-polymeric surfactant usually has a molecular weight below 1,000 dalton, in particular below 800 dalton. The non-polymeric surfactant may be non-ionic, anionic, cationic or zwitterionic. Suitable non-polymeric surfactants which may be used in the liquid compositions of the invention are disclosed, e.g. in "McCutcheon's Detergents and Emulsifiers Annual", MC Publishing Corp., Ridgewood, N.J., USA 1981; H. Stache, "Tensid-Taschenbuch", $2^{nd}$ ed., C. Hanser, Munich, Vienna, 1981; M. and J. Ash, "Encyclopedia of Surfactants", vol. I-III, Chemical Publishing Co., New York, N.Y., USA 1980-1981.

Examples of non-polymeric surfactants comprise
anionic surfactants, selected from the salts, in particular the sodium, potassium calcium or ammonium salts of
alkylsulfonates, such as lauryl sulfonate, isotridecylsulfonate,
alkylsulfates, in particular fatty alcohol sulfates, such as lauryl sulfate, isotridecylsulfate, cetylsulfate, stearylsulfate
aryl- and alkylarylsulfonates, such as napthylsulfonate, dibutylnaphtylsulfonate, dodecyidiphenylether sulfonate, cumylsulfonate, nonylbenzenesulfonate, dodecylbenzene sulfonate;
sulfonates of fatty acids and fatty acid esters;
sulfates of fatty acids and fatty acid esters;
sulfates of ethoxylated alkanoles, such as sulfates of ethoxylated lauryl alcohol;
sulfates of alkoxylated alkylphenols;
alkylphosphates, $C_8$-$C_{16}$ alkylphosphates;
dialkylphosphates, $C_8$-$C_{16}$ dialkylphosphates;
dialkylesters of sulfosuccinic acid, such as dioctylsulfosuccinate,
acylsarcosinates,
fatty acids, such as stearates,
acylglutamates,
ligninsulfonates,
condensates of naphthalinesulfonic acid or phenolsulfonic acid with formaldehyde;
non-ionic surfactants, selected from the group of
ethoxylated alkanoles, in particular ethoxylated fatty alcohols and ethoxylated oxoalcohols, such as ethoxylated lauryl alcohol, ethoxylated isotridecanol, ethoxylated cetyl alcohol, ethoxylated stearyl alcohol, and esters thereof, such as acetates
ethoxylated alkylphenols, such as ethoxylated nonylphenyl, ethoxylated dodecylphenyl, ethoxylated isotridecylphenol and the esters thereof, e.g. the acetates
alkylglucosides and alkyl polygucosides,
ethoxylated alkylglucosides,
ethoxylated fatty amines,
ethoxylated fatty acids,
partial esters, such as mono-, di- and triesters of fatty acids with glycerine or Sorbitan, such as glycerine monostearate, sorbitanmonooleat, sorbitantristearat
ethoxylated esters of fatty acids with glycerine or sorbitan, such as ethoxylated glycerine monostearate
ethoxylates of vegetable oils or animal fats, such as corn oil ethoxylate, castor oil ethoxylate, tallow oil ethoxylate,
ethoxylates of fatty amines, fatty amides or of fatty acid diethanolamides
cationic surfactants, selected from the group of
quaternary ammonium compounds, in particular alkyltrimethylammonium salts and dialkyldimethylammonium salts, e.g. the halides, sulfates and alkylsulfates
Pyridinium salts, in particular alkylpyridinium salts e.g. the halides, sulfates and $C_1$-$C_4$-alkylsulfates and
Imidazolinium salts in particular N,N'-dialkylimidazolinium salts, e.g. the halides, sulfates or methoxulfates.

As regards the non-polymeric surfactants, the term "alkyl" as used herein and if not defined otherwise is a linear or branched alkyl group having from 4 to 30, preferably from 6 to 22 carbon atoms, e.g. n-hexyl, 1-methylpentyl, n-heptyl, n-octyl, 2-ethylhexyl, n-nonyl, n-decyl, 1-methylnonyl, 2-propylheptyl, n-dodecyl, 1-methyldodecyl, n-tridecyl, n-tetradecyl, n-pentadecyl, n-hexadecyl, n-heptadecyl, n-octadecyl, n-nonadecyl, n-eicosyl, and the like. The term "ethoxylated" means that OH-functions have been reacted with ethyleneoxide to form a oligoethyleneoxide group. The degree of ethoxylation (number average of ethyleneoxide repeating units) will usually be in the range from 1 to 30 and in particular from 2 to 20.

The composition of the invention may further contain customary auxiliaries, such as defoamers, thickeners, preservatives, colorants, stabilizers, adjuvants, wetting agents, penetrants, coupling agents and the like which are usually employed in non-aqueous formulations of pesticides. A skilled person will appreciate that some of the aforementioned components, e.g. surfactants and solvents, may also work as auxiliaries. In particular, solvents may work as antifreeze agents or penetrants and the aforementioned surfactants may work as adjuvants or wetting agents.

Suitable thickening agents include inorganic thickening agents, such as clays, hydrated magnesium silicates and organic thickening agents, such as polysaccharide gums, like xanthan gum, guar gum, gum arabic and cellulose derivatives. Organic thickening agents are employed in amounts of from 0.5 to 30 g/l and preferably from 1 to 10 g/l while inorganic thickening agents are employed in amounts of from 0.5 to 30 g/l and preferably from 1 to 10 g/l.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. In general, the amount of preservatives will be from 0.1 to 10 g/l.

Suitable defoamers include polysiloxanes, such as polydimethyl siloxane. Defoamers are usually employed in amounts of from 0.1 to 5 g/l.

Suitable stabilizers comprise e.g. UV-absorbers such as cinnamic esters, 3,3-diphenyl-2-cyano acrylates, hydroxy and/or alkoxy substituted benzophenones, N-(hydroxyphenyl)-benzotriazoles, hydroxyphenyl-s-triazines, oxalic amides and salicylates, e.g. the UVINUL® 3000, 3008, 3040, 3048, 3049, 3050, 3030, 3035, 3039, 3088, UVINUL® MC80 and radical scavengers, e.g. ascorbic acid, sterically hindered amines (HALS-compounds) such as UVINUL® 4049H, 4050H and 5050H, and the like and anti-oxidants such as vitamin E. In general, the amount of stabilizer will be from 0.01 to 10 g/l of the concentrate composition.

These customary auxiliaries may be contained within the composition of the present invention. However, it is also possible to add these auxiliaries after dilution with water to the ready-to-use aqueous composition.

Upon dilution with water, the liquid compositions of the invention form an aqueous pesticide composition which contains the at least one organic pesticide compound C, the at least one organic solvent S, the at least one non-ionic block-copolymer P and optionally one or more non-polymeric surfactants and water. In these compositions, the at least one organic pesticide compound is present in the form of finely divided particles having a particle size in the nm range, i.e. the average particle size as determined by dynamic light scattering (at 25° C. and 1,013 mbar) is below 500 nm, preferably in the range from 100 to 300 nm, in particular in the range from 10 to 200 nm and most preferably in the range from 10 to 100 nm.

In order to obtain these aqueous pesticide compositions, the liquid compositions of the invention are usually diluted with at least 5 parts of water, preferably at least 10 parts of water, in particular at least 20 parts of water and more preferably at least 50 parts of water, e.g. from 10 to 10,000, in particular from 20 to 1,000 and more preferably from 50 to 250 parts of water per one part of the liquid composition (all parts are given in parts by weight).

Dilution will be usually achieved by pouring the concentrate compositions of the invention into water. Usually, dilution is achieved with agitation, e.g. with stirring, to ensure a rapid mixing of the concentrate in water. However, agitation is not necessary. Though the temperature of mixing is not critical, mixing is usually performed at temperatures ranging from 0 to 100° C., in particular from 10 to 50° C. or at ambient temperature.

The water used for mixing is usually tap water. However the water may already contain water soluble compounds which are used in plant protection, e.g. nutrificants, fertilizers or water soluble pesticides.

The aqueous pesticide compositions of the invention can be used as such for plant protection, i.e. for combating organisms that are harmful to plants or for protecting crops from attack or infestation by such an harmful organism. Therefore, the present invention also relates to an aqueous pesticide composition which is obtained by diluting the liquid concentrate composition of the present invention. The present invention also relates to the use of the aqueous pesticide compositions for plant protection and in particular to a method of combating organisms that are harmful to plants such as weeds, fungi, insects, arachnids or nematodes, which comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of an aqueous composition as described herein. The invention also relates to a method for protecting crops from attack or infestation by harmful organisms such as weeds, fungi, insects, arachnids or nematodes, which comprises contacting a crop with an effective amount of an aqueous composition as described herein.

The compositions of the invention after dilution are applied by usual means which are familiar to a skilled person.

If the composition contain a fungicide compound they may be applied against the following harmful fungi:

*Alternaria* species on vegetables and fruit and rice,

*Bipolaris* and *Drechslera* species on cereals, rice and turf,

*Blumeria graminis* (powdery mildew) on cereals,

*Botrytis cinerea* (gray mold) on strawberries, vegetables, ornamentals and grapevines,

*Erysiphe cichoracearum* and *Sphaerotheca fuliginea* on cucurbits,

*Fusarium* and *Verticillium* species on various plants,

*Mycosphaerella* species on cereals, bananas and peanuts,

*Phakopsara pachyrhizi* and *Phakopsara meibomiae* on soybeans

*Phytophthora infestans* on potatoes and tomatoes,

*Plasmopara viticola* on grapevines,

*Podosphaera leucotricha* on apples,

*Pseudocercosporella herpotrichoides* on wheat and barley,

*Pseudoperonospora* species on hops and cucumbers,

*Puccinia* species on cereals,

*Pyricularia oryzae, Cochliobolus miyabeanus* and *Corticium sasakii (Rhizoctonia solani), Fusarium semitectum* (and/or *moniliforme*), Helminth. Spp, *Cercospora oryzae, Cochliobolus miyabeanus, Sarocladium oryzae, S attenuatum, Entyloma oryzae, Gibberella fujikuroi* (bakanae), Grainstaining complex (various pathogens), *Bipolaris* species, *Drechslera* species, Agaricomycetidae such as *Rhizoctonia solani* and/or *Pythium* on rice,

*Rhizoctonia* species on cotton, rice and turf,

*Septoria tritici* and *Stagonospora nodorum* on wheat,

*Uncinula necator* on grapevines,

*Ustilago* species on cereals and sugar cane, and

*Venturia* species (scab) on apples and pears;

*Paecilomyces variotii* on materials (e.g. wood)

If the composition contain a compound, having insecticidal, acaricidal or nematicidal activity they may be applied against the following pest:

Insects from the order of the lepidopterans (*Lepidoptera*), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (*Coleoptera*), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica* 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, dipterans (*Diptera*), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifoli, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, thrips (*Thysanoptera*), e.g. *Frankliniella fusca, Frankliniella occidentalis, Frankliniella tritici, Scirtothrips citri, Thrips oryzae, Thrips palmi* and *Thrips tabaci*, hymenopterans (*Hymenoptera*), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta*, heteropterans (*Heteroptera*), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, homopterans (*Homoptera*), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiand*, and *Viteus vitifolii;* termites (*Isoptera*), e.g. *Calotermes flavicollis, Leucotermes flavipes, Reticulitermes lucifugus* und *Termes natalensis;* orthopterans (*Orthoptera*), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (*Acarina*), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Omithodorus moubata, Otobius megnini, Dermanyssus gallinae, Psoroptes ovis, Rhipicephalus appendiculatus, Rhipicephalus evertsi, Sarcoptes scabiei*, and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus*

*telarius* and *Tetranychus urticae, Panonychus ulmi, Panonychus citri*, and *oligonychus pratensis;*

Nematodes, especially plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species;

If the compositions according to the invention contain an insecticide compound which is active against rice pathogens, the composition may also be used to combat rice phatogens such as rice water weevil (*Lissorhoptrus oryzaphilus*), rice stem borer (*Chilo suppresalis*), rice leaf roller, rice leaf beetle, rice leaf miner (*Agromyca oryzae*), leafhoppers (*Nephotettix* spp.; especially smaller brown leafhopper, green rice leafhopper), planthoppers (Delphacidae; especially white backed planthopper, brown rice planthopper), stinkbugs.

If the compositions according to the invention contain a herbicide compound it will be used to control undesired vegetation. The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

The compositions containing a herbicide can be applied in conventional manner, usually as an aqueous composition which is obtained from a composition of the invention by diluting with water.

The required application rate of the pure active compounds without formulation auxiliary, depends on the density of the undesired vegetation, on the development stage of the plants, on the climatic conditions of the location where the composition is used and on the application method. In general, the application rate is from 0.001 to 3 kg/ha, preferably from 0.005 to 2 kg/ha and in particular from 0.01 to 1 kg/ha, from 0.1 g/ha to 1 kg/ha, from 1 g/ha to 500 g/ha or from 5 g/ha to 500 g/ha of active substance.

The diluted compositions are applied to the plants mainly by spraying, in particular foliar spraying. Application can be carried out by customary spraying techniques using, for example, water as carrier and spray liquor rates of from about 100 to 1 000 l/ha (for example from 300 to 400 l/ha). Application of the preparations by the low-volume and the ultra-low-volume method is possible, as is their application in the form of microgranules.

In a preferred embodiment of the invention, composition of active ingredients are applied in a rate which provides control of weeds or crops, in particular post-emergence to the weed or crop, but preferably prior to the planting, seeding or emergence of a desired crop.

In another preferred embodiment of the invention, control of weeds or crops is provided by an application of the composition of active ingredients before a desired crop is seeded, planted or emerged (pre-emergence or pre-plant application), followed by one or more treatments after the crop is emerged with one or more herbicides which are selective in the crop.

Moreover, it may be useful to apply the compositions according to the invention jointly as a mixture with other crop protection products, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

In a further embodiment of the invention, the compositions contain a compound, in particular an insecticide compound which is active against non-crop pests. Therefore the invention also relates to a method for controlling non-crop pests comprising contacting the pests or their food supply, habitat, breeding grounds or their locus with formulation according to the invention comprising at least an insecticide.

The invention further relates to the use of a composition according to the invention comprising at least an insecticide for the protection of non-living organic materials against non-crop pests.

Non-crop pests are pests of the classes Chilopoda and Diplopoda and of the orders Isoptera, Diptera, Blattaria (Blattodea), Dermaptera, Hemiptera, Hymenoptera, Orthoptera, Siphonaptera, Thysanura, Phthiraptera, Araneida, Parasitiformes and Acaridida, for example:

centipedes (Chilopoda), e.g. *Scutigera coleoptrata,*
millipedes (Diplopoda), e.g. *Narceus* spp.,
spiders (Araneida), e.g. *Latrodectus mactans*, and *Loxosceles reclusa,*
scabies (Acaridida): e.g. *sarcoptes* sp,
ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi,*

*Ornithodorus turicata* and parasitic mites (Mesostigmata), e.g. *Ornithonyssus bacoti* and *Dermanyssus gallinae*, termites (Isoptera), e.g. *Calotermes flavicollis, Leucotermes flavipes, Heterotermes aureus, Reticulitermes flavipes, Reticulitermes virginicus, Reticulitermes lucifugus, Termes natalensis*, and *Coptotermes formosanus*, cockroaches (Blattaria-Blattodea), e.g. *Blattelia germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inomata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, Earwigs (Dermaptera), e.g. *forficula auricularia*, true bugs (Hemiptera), e.g. *Cimex lectularius, Cimex hemipterus, Reduvius senilis, Triatoma* spp., *Rhodnius prolixus*, and *Arilus critatus*, ants, bees, wasps, sawflies (Hymenoptera), e.g. *Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus*, and *Linepithema humile*, crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera*, and *Locustana pardalina*, fleas (Siphonaptera), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

For examples, formulation according to the invention comprising at least an insecticide can be used for the protection of non-living organic materials, including but are not limited to house-hold goods such as fats, oils, mono- oligo- or polyorganosaccharides, proteins, or fresh or decaying fruits; cellulose-containing materials e.g. wooden materials such as houses, trees, board fences, or sleepers and also paper; and also construction materials, furniture, leathers, animal, plant and synthetic fibers, vinyl articles, electric wires and cables as well as styrene foams.

Furthermore, a formulation according to the invention comprising at least an insecticide can be used for the protection of non-living organic materials against non-crop pests selected from the group consisting of the class Diplopoda and of the orders Isoptera, Diptera, Blattaria (Blattodea), Dermaptera, Hemiptera, Hymenoptera, Orthoptera, and Thysanura.

The present invention also relates to a method for the protection of non-living organic materials against non-crop pests as mentioned above comprising contacting the pests or their food supply, habitat, breeding grounds, their locus or the non-living organic materials themselves with a pesticidally effective amount of a formulation according to the invention.

Furthermore, a formulation according to the invention comprising at least an insecticide can be used for protecting cellulose-containing non-living organic materials, e.g. for protecting cellulose-containing non-living organic materials against non-crop pests from the Isoptera, Diptera, Blattaria (Blattodea), Hymenoptera, and Orthoptera orders, most preferably the Isoptera orders.

The present invention also provides a method for protecting cellulose-containing non-living organic materials against non-crop pests, preferably from the Isoptera, Diptera, Blattaria (Blattodea), Hymenoptera, and Orthoptera orders, most preferably the Isoptera orders, comprising contacting the pests or their food supply, habitat, breeding grounds, their locus or the cellulose-containing non-living organic materials themselves with a a formulation according to the invention comprising at least an insecticide.

Furthermore, a formulation according to the invention comprising at least an insecticide can be used for protecting mono- oligo- or polysaccharides and proteins.

Furthermore, a formulation according to the invention comprising at least an insecticide can be used for protection of mono- oligo- or polysaccharides and proteins against non-crop pests selected from the Dermaptera, Diplopoda, Isoptera, Diptera, Blattaria (Blattodea), Hymenoptera, Orthoptera and Tysanura orders, most preferably the Isoptera, Diptera, Blattaria (Blattodea), and Hymenoptra orders.

Furthermore, a composition according to the invention comprising at least an insecticide can be used for used for protection of animals against non-crop pest of the class Chilopoda, and of the orders Araneida, Hemiptera, Diptera, Phthiraptera, Siphonaptera, Parasitiformes and Acaridida by treatment of the pests in water bodies and/or in and around buildings, including but not limited to walls, ground, manure piles, turf grass, pastures, sewers and materials used in the construction of buildings and also mattresses and bedding, with a formulation according to the present invention.

Animals include warm-blooded animals, including humans and fish. Thus, a formulation according to the invention comprising at least an insecticide can be used for protection of warm-blooded animals such as cattle, sheep, swine, camels, deer, horses, poultry, rabbits, goats, dogs and cats.

Furthermore, a formulation according to the invention comprising at least an insecticide can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). A formulation according to the invention comprising at least an insecticide can be are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant control composition of the present invention is directly applied to the nest of the ants or to its surrounding or via bait contact.

Furthermore, a formulation according to the invention comprising at least an insecticide can be applied preventively to places at which occurrence of the pests is expected.

If the formulation according to the present invention is intended for seed treatment purposes, the formulation may optionally comprise also pigments. Suitable pigments or dyes for seed treatment formulations are pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The invention furthermore comprises seeds treated with the formulation according to the present invention.

Suitable seeds are for example various crop seeds, fruit species, vegetables, spices and ornamental seed, for example corn/maize (sweet and field), durum wheat, soybean, wheat, barley, oats, rye, triticale, bananas, rice, cotton, sunflower, potatoes, pasture, alfalfa, grasses, turf, sorghum, rapeseed, Brassica spp., sugar beet, eggplants, tomato, lettuce, iceberg lettuce, pepper, cucumber, squash, melon, bean, dry-beans, peas, leek, garlic, onion, cabbage, carrot, tuber such as sugar cane, tobacco, coffee, turf and forage, cruciferous, cucurbits, grapevines, pepper, fodder beet, oil seed rape, pansy, impatiens, petunia and geranium.

The following examples are intended to further illustrate the present invention.

I Analytics:

Particle sizes were determined by dynamic light scattering with a "Nicomp by Particle Sizing System PSS, Model 370 at 25° C.

II. Preparation of the Compositions of the Invention:

1. In the Tables 1 to 14, the following abbreviations are used:
semicarbazone: 1-[N-(4-Trifluoromethoxyphenyl)semicarbazono]-1-(3-cyanophenyl)-2-(4-trifluoromethylphenyl)ethane (Metaflumizone)

amidrazone I:

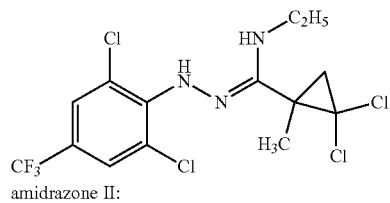

amidrazone II:

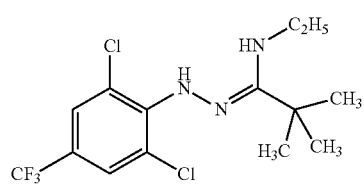

$M_N$ is the number average molecular weight blockcopolymer $P^a$: EO/PO triblockoopolymer, OH terminated; $M_N$ 4960, EO/PO ratio 43:57, HLB-Value 9;

blockoopolymer $P^b$: EO/PO triblockcopolymer, OH terminated; $M_N$ 3650, EO/PO ratio 25:75, HLB-Value 6;

blockcopolymer $P^c$: EO/PO triblockoopolymer, OH terminated; $M_N$ 2500, EO/PO ratio 25:75, HLB-Value 9;

blockcopolymer $P^d$: EO/PO triblockoopolymer, OH terminated; $M_N$ 5750, EO/PO ratio 43:57, HLB-Value 8;

blockcopolymer $P^e$: EO/PO triblockoopolymer, OH terminated; $M_N$ 4500, EO/PO ratio 50:50, HLB-Value 15;

blockcopolymer $P^f$: EO/PO triblockoopolymer, OH terminated; $M_N$ 2900, EO/PO ratio 66:34, HLB-Value 15;

blockcopolymer $P^g$: EO/PO triblockoopolymer, OH terminated; $M_N$ 4460, EO/PO ratio 43:57, HLB-Value 9.

blockcopolymer $P^h$: EO/PO triblockcopolymer, $M_N$ 6000, EO/PO ratio 60:40, blockcopolymer $P^i$: EO/PO triblockcopolymer, $M_N$ 4290, EO/PO ratio 30:70, HLB-Value 9.

blockcopolymer $P^k$: EO/PO triblockcopolymer, $M_N$ 7500, EO/PO ratio 60:40, blockcopolymer $P^m$: EO/PO triblockoopolymer, $M_N$ 4200, EO/PO ratio 40:60, HLB-Value 12-18.

II.1 Compositions 1.1-1.7, 2.1-2.8, 3.1-3.2, 4.1-4.9, 5.1-5.12, 6, 1-6.10, 7.1-7.9 and 8.1

General Procedure A:

The active ingredient and optionally further additives are stirred in the solvent S at room temperature until complete dissolution. The thus obtained solution is mixed with blockcopolymer P and optionally further surfactant until a homogenous mixture is obtained.

General Procedure B:

The active ingredient and optionally further additives are stirred in a mixture of the solvent S and the blockcopolymer P at room temperature until complete dissolution.

The compositions outlined in Tables 1, 3, 4, 5, 6, 7 and 8 were prepared by the general procedure A. The compositions outlined in Table 2 were prepared by the general procedure B. In Tables 1 to 8 the amounts of the ingredients are given in % by weight.

Upon dilution with water (100 parts per 1 part of composition) the compositions of Tables 1 to 8 form bluish clear compositions, wherein the active ingredient particles have an average diameter below 100 nm (as determined by quasi elastic light scattering). The diluted composition remain stable for at least 24 h. A diluted composition is estimated to be stable period of time if the particle size remains below 100 nm within said time period.

TABLE 1

Compositions containing 1-[N-(4-Trifluoromethoxyphenyl)semicarbazono]-1-(3-cyanophenyl)-2-(4-trifluoromethylphenyl)ethane (metaflumizone) (compositions 1.1 to 1.7):

| | composition | | | | | | |
|---|---|---|---|---|---|---|---|
| | 1.1 | 1.2 | 1.3 | 1.4 | 1.5 | 1.6 | 1.7 |
| Metaflumizone | 13.4 | 13.4 | 13.4 | 13.4 | 13.4 | 13.4 | 13.4 |
| γ-butyrolactone | 50.8 | — | — | 49.8 | 49.8 | 48.8 | — |
| acetone | — | 50.8 | 56.6 | — | — | — | 51.8 |
| blockcopolymer $P^a$ | — | — | 10.0 | — | — | — | 34.8 |
| blockcopolymer $P^b$ | 21.6 | 21.6 | — | 21.6 | 21.6 | 21.6 | — |
| blockcopolymer $P^c$ | 14.2 | 14.2 | 10.0 | 14.2 | 14.2 | 14.2 | — |
| Vitamin E | — | — | — | 1.0 | — | 1.0 | — |
| UV-absorber | — | — | — | — | 1.0 | 1.0 | — |

TABLE 2

Compositions containing methyl N-{2-[1-(4-chlorophenyl)-1H-pyrazol-3-yloxymethyl]phenyl}(N-methoxy)carbamate (Pyraclostrobin)

| | composition | | | | | | | |
|---|---|---|---|---|---|---|---|---|
| | 2.1 | 2.2 | 2.3 | 2.4 | 2.5 | 2.6 | 2.7 | 2.8 |
| pyraclostrobin | 12.0 | 24.0 | 36.0 | 24.0 | 24.0 | 24.0 | 24.0 | 24.0 |
| γ-butyrolactone | 58.0 | 36.0 | 24.0 | — | — | — | — | 51.0 |
| 2-pyrrolidone | — | — | — | 36.0 | — | — | — | — |
| N-methyl pyrrolidin-2-one | — | — | — | — | 36.0 | — | — | — |
| ethanol | — | — | — | — | — | 36.0 | — | — |
| acetone | — | — | — | — | — | — | 36 | — |
| blockcopolymer $P^a$ | 25.0 | 25.0 | 25.0 | 25.0 | 25.0 | 25.0 | 25.0 | 25.0 |
| blockcopolymer $P^b$ | 10.0 | 15.0 | 15.0 | 15.0 | 15.0 | 15.0 | 15.0 | — |

TABLE 3

Compositions containing methyl N-{2-[1-(4-chlorophenyl)-1H-pyrazol-3-yloxymethyl]phenyl}(N-methoxy)carbamate (Pyraclostrobin) and 2-chloro-N-(4'-chlorobiphenyl-2-yl)nicotinamide (Boscalid)

| | composition | |
|---|---|---|
| | 3.1 | 3.2 |
| boscalid | 12.0 | 12.0 |
| pyraclostrobin | 12.0 | 6.0 |
| N-methyl pyrrolidin-2-one | 46.0 | 46.0 |
| blockcopolymer $P^a$ | 20.0 | 20.0 |
| blockcopolymer $P^b$ | 10.0 | 16.0 |

TABLE 4

Compositions containing N-(1-ethylpropyl)-2,6-dinitro-3,4-xylidine (pendimethalin)

| | composition | | | | | | | | |
|---|---|---|---|---|---|---|---|---|---|
| | 4.1 | 4.2 | 4.3 | 4.4 | 4.5 | 4.6 | 4.7 | 4.8 | 4.9 |
| pendimethalin | 12.0 | 24.0 | 36.0 | 12.0 | 24.0 | 36.0 | 12.0 | 24.0 | 36.0 |
| γ-butyrolactone | 58.0 | 46.0 | 34.0 | — | — | — | — | — | — |
| diethylene glycol monomethylether | — | — | — | 58.0 | 46.0 | 34.0 | — | — | — |
| acetone | — | — | — | — | — | — | 58.0 | 46.0 | 34.0 |
| blockcopolymer $P^a$ | 10.0 | 10.0 | 10.0 | 10.0 | 10.0 | 10.0 | 10.0 | 10.0 | 10.0 |
| blockcopolymer $P^b$ | 10.0 | 10.0 | 10.0 | 10.0 | 10.0 | 10.0 | 10.0 | 10.0 | 10.0 |
| blockcopolymer $P^c$ | 10.0 | 10.0 | 10.0 | 10.0 | 10.0 | 10.0 | 10.0 | 10.0 | 10.0 |

TABLE 5

Compositions containing (RS)-2-chloro-N-(2,4-dimethyl-3-thienyl)-N-(2-methoxy-1-methylethyl)acetamide (dimethenamid)

| | composition | | | | | |
|---|---|---|---|---|---|---|
| | 5.1 | 5.2 | 5.3 | 5.4 | 5.5 | 5.6 |
| dimethenamid | 24.0 | 36.0 | 24.0 | 36.0 | 24.0 | 36.0 |
| γ-butyrolactone | 46.0 | 34.0 | — | — | — | — |
| propan-1,3-diol | — | — | 46.0 | 34.0 | — | — |
| diisopropanolamine | — | — | — | — | 46.0 | 34.0 |
| diethylene glycol monomethylether | — | — | — | — | — | — |
| ethanol | — | — | — | — | — | — |
| acetone | — | — | — | — | — | — |
| blockcopolymer $P^a$ | 10.0 | 10.0 | 10.0 | 10.0 | 10.0 | 10.0 |
| blockcopolymer $P^b$ | 10.0 | 10.0 | 10.0 | 10.0 | 10.0 | 10.0 |

TABLE 5-continued

Compositions containing (RS)-2-chloro-N-(2,4-dimethyl-3-thienyl)-N-(2-methoxy-1-methylethyl)acetamide (dimethenamid)

| blockcopolymer $P^c$ | 10.0 | 10.0 | 10.0 | 10.0 | 10.0 | 10.0 |
|---|---|---|---|---|---|---|

| | composition | | | | | |
|---|---|---|---|---|---|---|
| | 5.7 | 5.8 | 5.9 | 5.10 | 5.11 | 5.12 |
| dimethenamid | 24.0 | 36.0 | 24.0 | 36.0 | 24.0 | 36.0 |
| γ-butyrolactone | — | — | — | — | — | — |
| propan-1,3-diol | — | — | — | — | — | — |
| diisopropanolamine | — | — | — | — | — | — |
| diethylene glycol | 46.0 | 34.0 | — | — | — | — |

TABLE 5-continued

Compositions containing (RS)-2-chloro-N-(2,4-dimethyl-3-thienyl)-N-(2-methoxy-1-methylethyl)acetamide (dimethenamid)

| | | | | | | |
|---|---|---|---|---|---|---|
| monomethylether | | | | | | |
| ethanol | — | — | 46.0 | 34.0 | — | — |
| acetone | — | — | — | — | 46.0 | 34.0 |
| blockcopolymer $P^a$ | 10.0 | 10.0 | 10.0 | 10.0 | 10.0 | 10.0 |
| blockcopolymer $P^b$ | 10.0 | 10.0 | 10.0 | 10.0 | 10.0 | 10.0 |
| blockcopolymer $P^c$ | 10.0 | 10.0 | 10.0 | 10.0 | 10.0 | 10.0 |

TABLE 6

Compositions containing ethyl trichloro-2-pyridyloxyacetate (triclopyr-ethyl)

| | composition | | | | | |
|---|---|---|---|---|---|---|
| | 6.1 | 6.2 | 6.3 | 6.4 | 6.5 | 6.6 |
| triclopyr ethyl | 24.0 | 36.0 | 24.0 | 36.0 | 24.0 | 36.0 |
| acetone | 46.0 | 34.0 | — | — | — | — |
| γ-butyrolactone | — | — | 46.0 | 34.0 | — | — |
| 2-pyrrolidinone | — | — | — | — | 46.0 | 34.0 |
| diethylene glycol monomethylether | — | — | — | — | — | — |
| ethanol | — | — | — | — | — | — |
| blockcopolymer $P^a$ | 10.0 | 10.0 | 10.0 | 10.0 | 10.0 | 10.0 |
| blockcopolymer $p^b$ | 10.0 | 10.0 | 10.0 | 10.0 | 10.0 | 10.0 |
| blockcopolymer $P^c$ | 10.0 | 10.0 | 10.0 | 10.0 | 10.0 | 10.0 |

| | composition | | | |
|---|---|---|---|---|
| | 6.7 | 6.8 | 6.9 | 6.10 |
| triclopyr ethyl | 24.0 | 36.0 | 24.0 | 36.0 |
| acetone | — | — | — | — |
| γ-butyrolactone | — | — | — | — |
| 2-pyrrolidinone | — | — | — | — |
| diethylene glycol monomethylether | 46.0 | 34.0 | — | — |
| ethanol | — | — | 46.0 | 34.0 |
| blockcopolymer $P^a$ | 10.0 | 10.0 | 10.0 | 10.0 |
| blockcopolymer $P^b$ | 10.0 | 10.0 | 10.0 | 10.0 |
| blockcopolymer $P^c$ | 10.0 | 10.0 | 10.0 | 10.0 |

TABLE 7

Compositions containing α-cyano-3-phenoxybenzyl (1S,3S)-3-(2,2-dichlorovinyl)-2,2-dimethylcyclopropanecarboxylate (alpha-cypermethrin)

| | composition | | | | | | | | |
|---|---|---|---|---|---|---|---|---|---|
| | 7.1 | 7.2 | 7.3 | 7.4 | 7.5 | 7.6 | 7.7 | 7.8 | 7.9 |
| alpha-cypermethrin | 24.0 | 24.0 | 24.0 | 24.0 | 24.0 | 24.0 | 24.0 | 24.0 | 24.0 |
| acetone | 46.0 | — | — | — | — | — | — | — | — |
| γ-butyrolactone | — | 46.0 | — | — | — | — | — | 46.0 | — |
| 2-pyrrolidinone | — | — | 46.0 | — | — | — | — | — | 46.0 |
| diethylene glycol monomethylether | — | — | — | 46.0 | — | — | — | — | — |
| ethanol | — | — | — | — | 46.0 | — | — | — | — |
| cyclohexanone | — | — | — | — | — | 46.0 | 46.0 | — | — |
| blockcopolymer $P^a$ | 10.0 | 10.0 | 10.0 | 10.0 | 10.0 | 10.0 | 30.0 | 30.0 | 30.0 |
| blockcopolymer $P^b$ | 10.0 | 10.0 | 10.0 | 10.0 | 10.0 | 10.0 | — | — | — |
| blockcopolymer $P^c$ | 10.0 | 10.0 | 10.0 | 10.0 | 10.0 | 10.0 | — | — | — |

TABLE 8

Compositions containing 1-[4-(2-chloro-α,α,α-trifluoro-p-tolyloxy)-2-fluorophenyl]-3-(2,6-difluorobenzoyl)urea (flufenoxuron)

| | composition 8.1 |
|---|---|
| flufenoxuron | 6.0 |
| N-methyl pyrrolidin-2-one | 64.0 |
| blockcopolymer $P^a$ | 10.0 |
| blockcopolymer $P^b$ | 10.0 |
| blockcopolymer $P^c$ | 10.0 |

II.2 Compositions 9.1 to 9.6

Compositions 9.1 to 9.6 were prepared according to method A outlined in I.1 by dissolving 12.5 parts by weight of Metaflumizone in 62.5 parts by weight of γ-butyrolactone and adding thereto 25 parts by weight of blockcopolymer (blockcopolymer $P^b$ and/or blockcopolymer $P^c$ as given in Table 9).

Each of the compositions was diluted with 100 parts of water per 1 part of the composition (all parts given are parts by weight). The obtained compositions were analyzed within 24 h or 48 h, respectively, with regard to particle size of the dispersed active ingredient.

The relative amounts of blockcopolymer $P^b$ to blockcopolymer $P^c$ and the average particle sizes of the dispersed material after dilution with water are given in Table 9.

TABLE 9

| Composition | $P^b/P^{c\ 1)}$ | particle size [nm] | stability [2] |
|---|---|---|---|
| 9.1 | 0:10 | 48.2 | 24 h |
| 9.2 | 2:8 | 26.1 | 48 h |
| 9.3 | 4:6 | 21.7 | 48 h |
| 9.4 | 6:4 | 27.2 | 48 h |
| 9.5 | 8:2 | 41.9 | 48 h |
| 9.6 | 10:0 | 59.6 | 48 h |

[1] weight ratio of blockcopolymer $P^b$ to blockcopolymer $P^c$
[2] A composition is stable in the given time, if the particle size does not exceed 500 nm and no precipitate or crystalline material is observed.

II.3. Composition 10.1 to 10.5 of the Invention, Comparative Compositions A and B Compositions 10.1 to 10.5 were prepared according to method A outlined in I.1 by dissolving 10 parts by weight of Metaflumizone in 70 parts by weight of γ-butyrolactone and adding thereto 20 parts by weight of blockcopolymer as given in Table 10.

The type of blockcopolymer and the average particle sizes of the dispersed material after dilution with water are given in Table 10.

TABLE 10

| Composition | blockcopolymer | particle size [nm] | stability [2] |
|---|---|---|---|
| 10.1 | P$^d$ | 50 | 24 h |
| 10.2 | P$^a$ | 75 | 24 h |
| 10.3 | P$^e$ | 75 | 24 h |
| 10.4 | P$^f$ | 124 | 48 h |
| 10.5 | P$^b$ | 25 | 24 h |

[2] A composition is stable in the given time, if the particle size does not exceed 500 nm and no precipitate or crystalline material is observed.

For comparison two conventional non-aqueous compositions A and B containing 10% by weight of metaflumizone were prepared.

Composition A was a solution of 10 parts by weight of metaflumizone, and 25 parts by weight of an ethoxylated polyarylphenol of the formula $C_{30}H_{30}O(CH_2CH_2O)_n$ with n=14-18 in 65 parts by weight of a 1:1 mixture of N-methylpyrrolidin-2-one and cyclohexanone.

Composition B was a solution of 10 parts by weight of semicarbazone 90 parts by weight of acetone.

Upon dilution with 100 parts by weight of water per 1 part by weight of composition, composition A formed a suspension, wherein the initial average particle size of the dispersed material was about 0.25 μm. After 1 h the average particle size of the dispersed material was about 0.5 μm. After 24 h, large amounts of crystalline material of 2 mm in size were observed.

Upon dilution with 100 parts by weight of water per 1 part by weight of composition, composition B formed a suspension, wherein the initial average particle size of the dispersed material was about 0.5 μm. Small amounts of crystalline material were observed directly after dilution. After 1 h the average particle size of the dispersed material was about 1.0 μm. After 24 h, large amounts of crystalline material of 2 mm in size were observed.

II.3 Composition 11.1 to 11.19 of the Invention, Test on Dilution Stability 10 parts by weight of pesticide compound are dissolved in 65 parts by weight of solvent S. Thereto, 25 parts by weight of blockcopolymer P$^c$ are added. A clear solution is obtained. The active ingredient and the solvent is given in Table 11.

The thus obtained compositions were diluted with 100 parts by weight of water per 1 by weight part of composition. After 24 h, the diluted compositions were examined by dynamic light scattering. Each of the diluted compositions showed average particle sizes below 100 nm without formation of solids. Compositions rated ++++ showed average particle sizes below 20 nm while compositions rated +++ had average particle sizes between 20 nm and 100 nm.

TABLE 11

| | Active ingredient | Solvent S | Dilution stability after 24 h |
|---|---|---|---|
| 11.1 | Trichlopyr butoyl[1] | acetone | ++++ |
| 11.2 | Trichlopyr butoyl | γ-butyrolactone | ++++ |
| 11.3 | dimethenamid P | γ-butyrolactone | ++++ |
| 11.4 | dimethenamid P | propylene glycol | ++++ |
| 11.5 | dimethenamid P | diisopropanol amine | ++++ |
| 11.6 | Trichlopyr TEA[2] | 2-pyrrolidinone | ++++ |
| 11.7 | Trichlopyr TEA | diethylene glycol monomethylether | ++++ |
| 11.8 | Trichlopyr TEA | ethanol | ++++ |
| 11.9 | Pyraclostrobin | γ-butyrolactone | +++ |
| 11.10 | Pendimethaline | γ-butyrolactone | +++ |
| 11.11 | Ronilan[3] | γ-butyrolactone | +++ |
| 11.12 | metaflumizone | γ-butyrolactone | +++ |
| 11.13 | Pyraclostrobin | 2-pyrrolidinone | +++ |
| 11.14 | Pendimethaline | diethylene glycol monomethylether | +++ |
| 11.15 | dimethenamid P | diethylene glycol monomethylether | +++ |
| 11.16 | Pyraclostrobin | ethanol | +++ |
| 11.17 | dimethenamid P | ethanol | +++ |
| 11.18 | Trichlopyr TEA | Agrosol Ex 8[4] | +++ |
| 11.19 | Pyraclostrobin | acetone | +++ |
| 11.20 | Pendimethaline | acetone | +++ |
| 11.21 | dimethenamid P | acetone | +++ |

[1] 2-[(3,5,6-trichloro-2-pyridinyl)oxy]acetic acid 2-butoxyethyl ester
[2] 2-[(3,5,6-trichloro-2-pyridinyl)oxy]acetic acid triethylammonium salt
[3] vinclozolin
[4] N octyl pyrrolidin-2-one III. Investigation of Chemical Stability:

The following compositions were prepared in order to show the increased stability of compounds which may undergo chemical degradation in compositions according to the invention.

III.1 Chemical Stability of {[(isopropylidene)amino]oxy}acetic Acid, 2-methoxy-2-oxoethyl Ester (Oxime Ether)

The following composition C, D, E and F (comparative), 12.1 and 12.2 were prepared by mixing the active ingredients, solvents and surface active compounds given in Table 12a.

TABLE 12a

| | Composition | | | | | |
|---|---|---|---|---|---|---|
| | C | D | 12.1 | E | F | 12.2 |
| oxime ether [1] | 5 | 5 | 5 | 5 | 5 | 5 |
| Acetone | 85 | 85 | 85 | 68 | 68 | 68 |
| Water | — | — | — | 17 | 17 | 17 |
| Blockcopolymer P$^g$ | — | — | 10 | — | — | 10 |
| nonylphenol ethoxylate [2] | — | 7.5 | — | — | 7.5 | — |
| C$_8$-alkyl sulfosuccinate | — | 2.5 | — | — | 2.55 | — |

[1] {[(isopropylidene)amino]oxy}acetic acid, 2-methoxy-2-oxoethyl ester
[2] degree of ethoxylation EO = 8

The samples were stored at 50° C. and removed at weekly intervals for analysis of the degree of degradation (by normal phase HPLC, UV-detection). The data were fitted to a first order kinetic profile and the time for 10% degradation was calculated. The results are given in Table 12b.

TABLE 12b

| Composition | Time for 10% degradation [days] |
|---|---|
| C | 313.1 |
| D | >5000 |
| 11.1 | >5000 |
| E | 130.3 |

TABLE 12b-continued

| Composition | Time for 10% degradation [days] |
|---|---|
| F | 10.1 |
| 11.2 | 1169.2 |

III.2 Chemical Stability of Diflufenzopyr

The following composition G and H (comparative), 13.1 (inventive) were prepared by mixing the active ingredients, solvents and surface active compounds given in Table 13.

The samples were stored at 50° C. and removed at weekly intervals for analysis of the degree of degradation (by normal phase HPLC, UV-detection). The data were fitted to a first order kinetic profile and the time for 10% degradation was calculated. The results are given in Table 13.

TABLE 13

| | Composition | | |
|---|---|---|---|
| | G | H | 13.1 |
| diflufenzopyr-sodium | 5 | 5 | 5 |
| Acetone | 85 | 85 | 85 |
| Blockcopolymer $P^g$ | — | — | 10 |
| nonylphenol ethoxylate [1] | — | 7.5 | — |
| $C_8$-alkyl sulfosuccinate | — | 2.5 | — |
| Time for 10% degradation [days] | 4.2 | 1.1 | 54.1 |

[1] degree of ethoxylation EO = 8

III.3 Chemical Stability of Metaflumizone

The following compositions J (comparative) and 14.1 (inventive) were prepared by mixing the active ingredients, solvents and surface active compounds given in Table 14.

The samples were stored at 25° C. for 1 year. Then the content of active ingredient was determined by HPLC-Analysis. The results are given in Table 14.

TABLE 14

| | Composition | |
|---|---|---|
| | J | 14.1 |
| semicarbazone [1] | 12.5 | 12.5 |
| γ-Butyrolactone | 87.5 | 57.5 |
| Blockcopolymer $P^g$ | — | 30 |
| Recovery after 1 year [%] | 80.0 | 99.8 |

[1] 1-[N-(4-Trifluoromethoxyphenyl)semicarbazono]-1-(3-cyanophenyl)-2-(4-trifluoromethylphenyl)ethane

IV Biological Tests:
1. Biological Performance of Compositions Containing Metaflumizone:
1.1 Bioefficacy The following compositions K, L, and 15.1 were evaluated under field conditions:

K is a commercial aqueous suspension concentrate of metaflumizone, wherein the average particle size of the active ingredient after dilution is about 1 μm. K contains 22% by weight of metaflumizone and 10% by weight of surfactant which is a mixture of polyoxypropylene-polyoxyethylene-triblockcopolymer, sodium-dioctylsulfosuccinate, ethoxylated alkanol and ethoxylated alkylphenol.

L is a commercial aqueous suspension concentrate of metaflumizone wherein the average particle size of the active ingredient after dilution is about 1.6 μm. L contains 22% by weight of metaflumizone and 10% by weight of surfactant which is a mixture of polyoxypropylene-polyoxyethylene-triblockcopolymer, sodium-dioctylsulfosuccinate, ethoxylated alkanol and ethoxylated alkylphenol.

15.1 is a liquid concentrate composition according to the invention which contains 12.5% by weight of metaflumizone, 52.8% by weight of butyrolactone and 35% by weight of a blend of blockcopolymers $P^b$, $P^c$ and $P^g$. Upon dilution with water the average particle size was about 20 nm.

Each of the compositions K, L and 15.1 were diluted with water to a concentration of semicarbazone of 3500 ppm for 100% use rate.

The compositions were applied under field conditions at different use rates to plantations of several plant species of leafy and fruiting vegetables, including *brassica* crops, potatoes, soybean, tobacco, beets and cotton. The insecticidal activity against the following insect species:

Heliothisvirescens (tobacco budworm)
Helicoverpazea (cotton bollworm, tomato fruitworm, corn earworm)
Helicoverpa armigera (old world bollworm)
Spodopteraexigua (beet armyworm)
Pseudoplusiaincludens (soybean looper)
Spodopteraeridania (southern armyworm)
Spodopteraornithogalli (yellowstriped armyworm)
Spodopterapraefica (striped armyworm)
Spodoptera frugiperda (fall armyworm)
Mamestrabrassicae (cabbage armyworm)
Pierisrapae (imported cabbageworm)
Hellulaundalis (cabbage webworm)
Crocidolomiabinotalis (Asian cabbageworm)
Ostrinianubilalis (European corn borer)
Trichoplusiani (cabbage looper)
Plutellaxylostella (diamondback moth)
Keiferialycopersicella (tomato pinworm)
Alabama argillacea (cotton leafworm)
Anticarsia gemmatalis (velvetbean caterpillar)
Pectinophora gossypiella (pink bollworm)
Manduca quinquemaculata (tomato hornworm)
Grapholita molesta (oriental fruitmoth)
Leptinotarsadecemlineata (Colorado potato beetle)
Temnorhinusmendicus (sugarbeet weevil)
Chaetocnema, Phyllotreta & Psylliodes spp. (flea beetles)
Aulacophora spp. (pumpkin beetle)
Diabrotica spp. (rootworm spp.)
Phaedonbrassicae (leaf beetle)
Oulema spp. (cereal leaf beetle)

was assessed in 100 field trials and for each use rate the average activity against different insect species is categorically rated from 1 to 4.

3 is the standard activity achieved at 100% (standard) use rate for the commercial suspension concentrate K. Rating 4 exceeds standard control while 2 is worse than standard control and 1 is much worse than standard control. The results are given in Table 15.

TABLE 15

| | Average Activity of Composition | | |
|---|---|---|---|
| Use Rate [%][1] | K | L | 15.1 |
| 40 | n.d.[2] | n.d. | 2 |
| 60 | 1 | 1 | 3 |
| 70 | 2 | 2 | 4 |
| 85 | 3 | 3 | 4 |
| 100 | 3 | 3 | n.d. |

[1] % use rate of recommended use rate for commercial suspension concentrate K (corresponds to a concentration of 3500 ppm)
[2] n.d. no data VI. Compositions Containing N-ethyl-2,2-dichloro-1-methylcyclo-propanecarboxamide-2-(2,6-dichloro-α,α,α-trifluoro-p-tolyl)hydrazone (Amidrazone 1) or N-ethyl-2,2-di(methyl)propionamide-2-(2,6-dichloro-α,α,α-trifluoro-p-tolyl)-hydrazone (Amidrazone II) Compositions VI.1 to VI.52

VI.1 Preparation of Compositions VI.1 to VI.52

Compositions VI.1 to VI.52 were prepared according to the general methods A or B as described in II.1. The amounts of active ingredient (either amidrazone I or II), solvent, and blockcopolymer are given in table 16 in parts by weight.

TABLE 16

|  | VI.1 | VI.2 | VI.3 | VI.4 | VI.5 | VI.6 | VI.7 |
|---|---|---|---|---|---|---|---|
| amidrazone I | 10.7 | 10.7 | — | — | — | 11.0 | — |
| amidrazone II | — | — | 10.7 | 10.7 | 10.3 | — | 11.0 |
| blockcopolymer $P^h$ | 8.0 | — | 8.0 | — | — | 10.0 | 10.0 |
| blockcopolymer $P^i$ | 11.5 | 10.2 | 11.5 | 10.2 | — | 7.0 | 7.0 |
| blockcopolymer $P^k$ | 0.8 | 0.7 | 0.8 | 0.7 | 30.0 | 1.0 | 1.0 |
| blockcopolymer $P^m$ | — | 7.1 | — | 7.1 | — | — | — |
| γ-butyrolactone | 69.0 | 71.3 | 69.0 | 71.3 | — | 71.0 | 71 |
| propylene carbonate | — | — | — | — | 59.7 | — | — |

|  | VI.8 | VI.9 | VI.10 | VI.11 | VI.12 | VI.13 | VI.14 |
|---|---|---|---|---|---|---|---|
| amidrazone I | 11.0 | — | 10.0 | 10.0 | 10.0 | 10.0 | 20.0 |
| amidrazone II | — | 11.0 | — | — | — | — | — |
| blockcopolymer $P^h$ | 10.0 | 10.0 | — | 30.0 | — | 40.0 | — |
| blockcopolymer $P^i$ | — | — | — | — | — | — | — |
| blockcopolymer $P^k$ | 1.0 | 1.0 | 30.0 | — | 40.0 | — | — |
| blockcopolymer $P^m$ | 7.0 | 7.0 | — | — | — | — | 40.0 |
| γ-butyrolactone | 71.0 | 71 | — | — | — | — | — |
| propylene carbonate | — | — | 60.0 | 60.0 | 60.0 | 60.0 | 40.0 |

|  | VI.15 | VI.16 | VI.17 | VI.18 | VI.19 | VI.20 | VI.21 |
|---|---|---|---|---|---|---|---|
| amidrazone I | 20.0 | 10.0 | 10.0 | 20.0 | 10.0 | 10.0 | 10.0 |
| amidrazone II | — | — | — | — | — | — | — |
| blockcopolymer $P^h$ | 40 | — | — | — | — | — | 3.0 |
| blockcopolymer $P^i$ | — | — | — | — | — | — | — |
| blockcopolymer $P^k$ | — | 40.0 | 30.0 | 40.0 | — | 20.0 | — |
| blockcopolymer $P^m$ | — | — | — | — | 20.0 | — | 27 |
| γ-butyrolactone | — | — | — | — | — | — | — |
| propylene carbonate | 40.0 | 50.0 | 60.0 | 40.0 | 70.0 | 70.0 | 60.0 |

|  | VI.22 | VI.23 | VI.24 | VI.25 | VI.26 | VI.27 | VI.28 |
|---|---|---|---|---|---|---|---|
| amidrazone I | 10.0 | 10.0 | 10.0 | 10.0 | 10.0 | 10.0 | 10.0 |
| amidrazone II | — | — | — | — | — | — | — |
| blockcopolymer $P^h$ | 6.0 | 9.0 | 12.0 | 15.0 | 18.0 | 21.0 | 24.0 |
| blockcopolymer $P^i$ | — | — | — | — | — | — | — |
| blockcopolymer $P^k$ | — | — | — | — | — | — | — |
| blockcopolymer $P^m$ | 24.0 | 21.0 | 18.0 | 15.0 | 12.0 | 9.0 | 6.0 |
| γ-butyrolactone | — | — | — | — | — | — | — |
| propylene carbonate | 60.0 | 60.0 | 60.0 | 60.0 | 60.0 | 60.0 | 60.0 |

|  | VI.29 | VI.30 | VI.31 | VI.32 | VI.33 | VI.34 | VI.35 |
|---|---|---|---|---|---|---|---|
| amidrazone I | 10.0 | 10.0 | 10.0 | 10.0 | 10.0 | 10.0 | 20.0 |
| amidrazone II | — | — | — | — | — | — | — |
| blockcopolymer $P^h$ | 27.0 | 12.0 | 16.0 | 20.0 | 24.0 | 28.0 | 12.0 |
| blockcopolymer $P^i$ | — | — | — | — | — | — | — |
| blockcopolymer $P^k$ | — | — | — | — | — | — | — |
| blockcopolymer $P^m$ | 3.0 | 28.0 | 24.0 | 20.0 | 16.0 | 12.0 | 28.0 |
| γ-butyrolactone | — | — | — | — | — | — | — |
| propylene carbonate | 60.0 | 50.0 | 50.0 | 50.0 | 50.0 | 50.0 | 50.0 |

|  | VI.36 | VI.37 | VI.38 | VI.39 | VI.40 | VI.41 | VI.42 |
|---|---|---|---|---|---|---|---|
| amidrazone I | 20.0 | 20.0 | 20.0 | 10.0 | 10.0 | 15.0 | 10.0 |
| amidrazone II | — | — | — | — | — | — | — |
| blockcopolymer $P^h$ | 16.0 | 20.0 | 24.0 | 20.0 | — | — | — |

TABLE 16-continued

|  |  |  |  |  |  |  |  |
|---|---|---|---|---|---|---|---|
| blockcopolymer $P^i$ | — | — | — | — | — | — | — |
| blockcopolymer $P^k$ | — | — | — | — | 20.0 | 20.0 | 15.0 |
| blockcopolymer $P^m$ | 24.0 | 20.0 | 16.0 | 20.0 | 20.0 | 20.0 | 20.0 |
| γ-butyrolactone | — | — | — | — | — | — | — |
| propylene carbonate | 40.0 | 40.0 | 40.0 | 50.0 | 50.0 | 45.0 | 55.0 |

|  | VI.43 | VI.44 | VI.45 | VI.46 | VI.47 | VI.48 | VI.49 |
|---|---|---|---|---|---|---|---|
| amidrazone I | 10.0 | 10.0 | 20.0 | 10.0 | — | — | — |
| amidrazone II | — | — | — | — | 10.0 | 10.0 | 10.0 |
| blockcopolymer $P^h$ | — | — | — | — | — | 30.0 | — |
| blockcopolymer $P^i$ | — | — | — | — | — | — | — |
| blockcopolymer $P^k$ | 17.5 | 20.0 | 20.0 | 10.0 | — | — | 30.0 |
| blockcopolymer $P^m$ | 17.5 | 15.0 | 20.0 | 10.0 | 30.0 | — | — |
| γ-butyrolactone | — | — | — | — | — | — | — |
| propylene carbonate | 55.0 | 55.0 | 40.0 | 70.0 | 60.0 | 60.0 | 60.0 |

|  | VI.43 | VI.44 | VI.45 | VI.46 | VI.47 | VI.48 | VI.49 |
|---|---|---|---|---|---|---|---|
| amidrazone I | — | — | — | — | — | — | — |
| amidrazone II | 10.0 | 10.0 | 10.0 | 10.0 | 10.0 | 10.0 | 10.0 |
| blockcopolymer $P^h$ | 6.0 | 15.0 | 24.0 | — | — | — | 6.0 |
| blockcopolymer $P^i$ | — | — | — | — | — | — | — |
| blockcopolymer $P^k$ | — | — | — | 6.0 | 15.0 | 24.0 | 24.0 |
| blockcopolymer $P^m$ | 24.0 | 15.0 | 6.0 | 24.0 | 15.0 | 6.0 | — |
| γ-butyrolactone | — | — | — | — | — | — | — |
| propylene carbonate | 60.0 | 60.0 | 60.0 | 60.0 | 60.0 | 60.0 | 60.0 |

|  | VI.50 | VI.51 | VI.52 |
|---|---|---|---|
| amidrazone I | — | — | — |
| amidrazone II | 10.0 | 10.0 | 10.0 |
| blockoopolymer $P^h$ | 15.0 | 24.0 | — |
| blockoopolymer $P^i$ | — | — | — |
| blockoopolymer $P^k$ | 15.0 | 6.0 | 40 |
| blockoopolymer $P^m$ | — | — | — |
| γ-butyrolactone | — | — | — |
| propylene carbonate | 60.0 | 60.0 | 50.0 |

Upon dilution with water (100 parts per 1 part of composition) the compositions of table 16 form bluish clear compositions. The diluted composition remain stable for at least 24 h.

VI.2 Biological Tests of Compositions VI

1, Adult Insect Vial Contact Assays Against Adult Male German Cockroach, *Blattella germanica* (Bg), House Fly, *Musca domestica* (Md), and Acrobat Ant, *Crematogaster* sp. (Cre):

Glass vials (20 ml scintillation vials) were treated with a solution, obtained by diluting composition VI.2 or VI.4 with water. Treatments were made by placing 445 μl of solution into the bottom of each vial. Each vial was turned on its side and placed onto a commercial grade hot dog roller (APW/Wyott HRS-31) without applying any heat. The vials were allowed to roll (6 rpm), uncapped, for ca. 40-60 minutes to allow treatment to completely coat the vial and allowed for full drying of the water treatment. After drying, a small piece of cotton dental wick (ca. 5-7 mm wide), lightly moistened with 10% sugar water, was placed into the bottom of each vial to supply food and moisture for the insects. Test vials were held at room temperature (ca. 25° C.) and insects were observed for incapacitation at 4, 24, and 48 hours after treatment. The results are given in table 17:

TABLE 17

|  |  | Mean Percent Kd[2] | | |
|---|---|---|---|---|
| Treatment[1] | Hours post treatment | Md 1 ppm | Cre 1 ppm | Bg 5 ppm |
| VI.4 | 4 | 100 | 46.7 | 100 |
|  | 24 | 100 | 50 | 100 |
|  | 48 | 100 | 46.7 | 100 |

TABLE 17-continued

| Treatment[1] | Hours post treatment | Mean Percent Kd[2] | | |
|---|---|---|---|---|
| | | Md 1 ppm | Cre 1 ppm | Bg 5 ppm |
| VI.2 | 4 | 100 | 100 | 100 |
| | 24 | 100 | 100 | 100 |
| | 48 | 100 | 100 | 100 |
| Untreated | 4 | 0 | 0 | 0 |
| | 24 | 0 | 0 | 0 |
| | 48 | 3.3 | 0 | 13.3 |

[1]Test initiated Oct. 27, 2004 (Md, Cre), Oct. 26, 2004 (Bg).
[2]Mean is based on 6 insects per vial and 5 reps per treatment. 445 microliters trt/vial.

2. Soil Exposure Assays Against Workers of Eastern Subterranean Termite, *Reticulitermes flavipes*:

Test Arenas:

Tests were conducted in 60×15 mm plastic Petri dishes. The bottom of each dish was coated with 2 ml agar.

100 g of Princeton Sandy Loam Soil was incorporated on a weight-to-weight ratio of a.i. to soil in a 100 ml Qorpak jar. Incorporation consists of applying 7 ml of composition VI.2 or VI.4 diluted with water to the soil, and shaking the soil by hand to mix lightly then rolling the jar on a commercial roller for 30 minutes. After the jar had finished rolling, it was shaken by hand again and allowed to air dry over night. 2 g of incorporated soil was added per dish. 15 worker termites were introduced into each dish, and a piece of filter paper (¼×¼ in.) was added to each dish and moistened with a drop of distilled water for a food source. Mortality (dead), moribund (near death, unable to walk) and intoxicated (obviously impaired, but able to walk) readings were recorded daily for 9 days. The results are given in table 18:

TABLE 18

| Treatment[1] | Rate ppm a.i. (w/w) | Mean cumulative % mortality at days after treatment (DAT)[2] | | | | | |
|---|---|---|---|---|---|---|---|
| | | 1 DAT | 2 DAT | 4 DAT | 5 DAT | 7 DAT | 9 DAT |
| VI.2 | 5 | 93.3 | 100.0 | — | — | — | — |
| VI.2 | 10 | 100.0 | — | — | — | — | — |
| VI.4 | 5 | 32.0 | 40.0 | 64.0 | 66.7 | 69.3 | 80.0 |
| V.4 | 10 | 82.7 | 93.3 | 100.0 | — | — | — |
| Termidor SC[3] | 0.5 | 4.0 | 81.3 | 100.0 | — | — | — |
| Untreated Control | — | 0.0 | 1.3 | 1.3 | 2.7 | 4.0 | 4.0 |

[1]Bioassay initiated 03 Nov. 2004.
[2]Each mean is based on 75 termites (5 replications/treatment).
[3]Commercial Suspension concentrate of fipronil 3. Soil Tunneling Assays Against Workers of Eastern Subterranean Termite, *Reticulitermes flavipes*:

To observe the tunneling response of subterranean termites through treated soil arena tubes containing treated soil were prepared as described below. Termites were placed at one end of the tube and the tunneling subsequent mortality effects were evaluated.

Arena Preparation—

1. Tests were run in 1.5 cm diameter, transparent tubes (PVC tubes) which were cut at one end to a length of 13 to 14 cm. Any sharp points formed where the tube was cut were trimmed.
2. 5% agar was prepared and poured into glass Petri dishes to a depth of 1 cm.
3. A quantity of wood flour was prepared for use as an attractive food source at the bottom of the tunnel tubes. The hardwood samples will only require addition of enough water to thoroughly moisten the woodflour (sample should be wet but still loose enough for easy transfer into tubes). The softwood samples (pine) were pre-washed to remove residues of natural defensive chemicals. The softwood material was placed into a Buchner funnel (with filter paper) and water was added until sample was covered with standing water. The sample was allowed to soak for 30 min and then the water was drawn off with vacuum. Additional water as needed for required moisture content was added.
4. Test soil was prepared by drenching the soil with a solution, obtained by diluting composition VI.2 or VI.4 with water. The concentration of active ingredient in the soil is given in table 19.
5. The smooth (un-cut) end of each tube was pressed into the poured agar to load a 1 cm agar plug into the tube. The plug was pushed most of the way through the tube (approx. 3 cm from opposite end) with a wood dowel. Approx. 2 cm of woodflour were loaded into the short end of the tube, a rubber stopper was inserted and then the contents were firmly packed against the stopper.
6. A 5 cm length from the top of the agar plug was marked. The tube was held upright and loaded with pre-treated test soil to slightly above the 5 cm mark. The tube was lightly tapped on the counter top to compact the soil. Additional soil was loaded and compacting step was repeated to fill the 5 cm length with loosely compacted soil.
7. Using a second tube, another agar plug was cut, transferred into the tube with soil and packed down against the soil to complete the column assembly.
8. 30 termite workers were collected in a glass vial with 2 or 3 short strips of filter paper and transfered all to the top chamber of the completed soil tube. The tube was capped with cork or rubber stopper and stored in upright position in test tube racks. When testing with Formosan termites, the tubes were infested with 30 workers+3 soldiers.

Test Procedure:

The completed tubes were stored under standard holding conditions and observed daily for penetration of tunnels through the soil columns. Daily progress through the soil can be marked directly on the tube and measured later (see sample data array). Instinctive behavior for termites will be to immediately start tunneling downward for shelter and termites will usually penetrate through an untreated soil column in 24 to 48 hrs. Failure to penetrate into the soil column could be the result of repellent treatment in the soil or rapid toxicity.

The tubes were examined at 3 and 6 days for number of surviving termites. The contents of each tube were emptied onto a metal tray so that it could be spread out for easier location of surviving termites. The survivors were observed for symptoms of intoxication or moribundity and recorded on the data sheet. If the survivors show no sign of intoxication they were recorded as normal ("norm" on datasheet). Dead termites were usually not found due to rapid deterioration of the bodies in contact with the soil. Any termites not accounted for through direct observation were considered to be dead. The number dead recorded on datasheet were determined from the number of termites "not found" plus any dead bodies directly observed. The results are given in tables 19a and 19n:

TABLE 19a

| | Dead/intoxicated (Mean %) | | | | | |
|---|---|---|---|---|---|---|
| | VI.4 0.5 ppm | | VI.2 0.5 ppm | | Control (untreated) | |
| 3 DAT | 64 | 0 | 71 | 0 | 0 | 0 |
| 6 DAT | 96 | 0 | 100 | 0 | 0 | 0 |

TABLE 19b

| | Tunneling in cm (Mean %) | | |
|---|---|---|---|
| | VI.4 0.5 ppm | VI.2 0.5 ppm | Control (untreated) |
| 3 DAT | 4.6 | 4.6 | 5.0 |
| 6 DAT | 5.0 | 5.0 | 5.0 |

Termite tunneling was not affected by formulation type; i.e., they were all non-repellent. All formulations resulted in similar mortality at 3 DAT and 6 DAT.

4. Soil Surface Applied Contact Assays Against Argentine Ant, *Iridomyrmex humilis*:

Test Arenas:

Tests were conducted in 100×20 mm polystyrene Petri dish. The inner sides of the dishes were painted with Fluon (Northern Products, Woonsocket, R.I.) to prevent ant escape. Test arenas were prepared by dispensing a thin layer of 1% agar into the dishes and then spreading 10 g of Princeton Sandy Loam soil over the agar.

Test treatments were applied as solutions, obtained by diluting composition VI.2 or VI.4 with water. The solutions were sprayed @ 1 gal/1000 ft² with a DeVilbiss atomizer. Dish covers were used to conserve moisture and additional water added as needed. A small cotton dental wick was placed in each arena soaked with 20% sucrose solution for food and water source for the duration of test. 15 ants were placed in each dish, and each treatment was replicated three times. Test dishes were maintained in the laboratory (22° C.) and observed for mortality daily for 5 to 10 days.

All formulations performed equally and VI.4 resulted in 100% mortality by 2 DAT while formulation VI.2 resulted in 100% mortality at 3 DAT.

5. Ant Bait No-Choice Assays Against Argentine Ant, *Iridomyrmex humilis*:

Test Arenas:

Tests were conducted in 100×20 mm Petri dishes. The inner sides of the dishes were painted with Fluon (Northern Products, Woonsocket, R.I.) to prevent ant escape. Baits were mixed with a 40% honey/water solution. For honey/water incorporation, a stock solution containing 40% by weight of honey in distilled water was prepare.

For each treatment, compositions VI2. or VI.4 were diluted with water and then add to the honey water solution to bring the final solution up to the desired concentration of active ingredient and 40% honey water. For each test arena, 0.2 ml of treated honey water solution was applied to a micro weigh dish to hold the bait material. 15 ants were introduced into each test arena dish, starved for 24 hours before the introduction of the bait material. A water soaked dental wick was provided during the starvation period. The water soaked dental wick was removed upon the introduction of the bait solution. Test dishes were covered with the dish cover to maintain humidity, and maintained in laboratory (22° C.) and observed for mortality and intoxicating effects for 5 days.

Formulation VI.4 resulted in 100% mortality by 3 DAT. Formulation VI.2 resulted in 100% mortality by 5 DAT.

6. Roach Bait No-Choice Assays Against Adult Male German Cockroach, *Blattella germanica*:

Test Arenas:

Grease (3 parts petroleum jelly {Vaseline}, and 2 parts mineral oil) were placed on the top 3-4 cm of clear plastic Rubbermaid containers measuring 20 L×21 W×12 H cm to prevent the insects from escaping. Water was provided with a 4-dram glass vial with a dental wick half inserted into the vial. The vial was placed on its side to allow easy access for the roaches. The vial was refilled with water every 3-4 days.

Bait was prepared using ground cat chow and composition VI.2 or VI.4 was incorporated on a weight-to-weight ratio of a.i. to chow. For each treatment, a total of 1 gram of treated chow was prepared using a total volume of 1 ml of diluted composition to completely wet the chow with each rate of compound. The roaches were placed in test arenas and starved for 24 hours prior to bait introduction, with a water source at all times. Treatments were replicated three times. The amount of treated chow for each arena was weighed out to approximately 0.03 grams, and placed in a plastic weigh boat (45 mm×45 mm). Arenas were placed in the laboratory (22° C.) and covered with blotter paper. Mortality was observed for 3 days.

Both formulations resulted in 100% mortality by 3 DAT.

We claim:

1. A liquid pesticide concentrate composition, which comprises:
   a) 1 to 60% by weight, based on the total weight of the composition, of at least one organic pesticide compound C having a water solubility of not more than 5 g/l at 25° C./1013 mbar,
   b) 10 to 80% by weight, based on the total weight of the composition, of at least one organic solvent S having a water solubility of at least 10 g/l at 25° C./1013 mbar, and which is capable of dissolving the pesticide compound C,
   c) from 15 to 50% by weight, based on the total weight of the composition, of at least one non-ionic blockcopolymer P comprising at least one polyethyleneoxide moiety PEO and at least one polyether moiety PAO consisting of repeating units derived from $C_3$-$C_{10}$-alkyleneoxides and/or styrene oxide, wherein the non-ionic blockcopolymer P is characterized by an HLB-value ranging from 5 to 20, and wherein the non-ionic blockcopolymer has a number average molecular weight $M_N$ ranging from 1,000 to 100,000 Dalton;
   d) optionally from 0.1 to 10% by weight, based on the total weight of the composition, of one or more non-polymeric surfactants,
   e) wherein the weight ratio of the non-ionic blockcopolymer to the organic pesticide compound P:C is from 0.6:1 to 10:1 and wherein the components a), b), c) and optionally d) make up at least 95% of the composition, provided that if water is present in the composition, the weight ratio of water to solvent S does not exceed 1:5.

2. The composition as claimed in claim 1, wherein the non-ionic blockcopolymer has a number average molecular weight $M_N$ ranging from 2,500 to 50,000 Dalton.

3. The composition as claimed in claim 1, wherein the PEO and the PAO moieties make up at least 80% by weight of the non-ionic blockcopolymer P.

4. The composition as claimed in claim 1, wherein the weight ratio of PEO moieties to PAO moieties in the non-ionic blockcopolymer ranges from 1:10 to 10:1.

5. The composition as claimed in claim 1, wherein the non-ionic blockcopolymer is selected from the group of polymers having the following formulae P1 to P5:

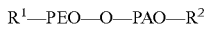  P1

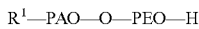  P2

  P3

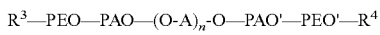  P4

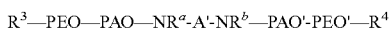  P5 wherein n is 0 or 1,

A, A' are a bivalent organic radical which has 2 to 20 carbon atoms and which may carry 1 or 2 hydroxy groups and/or 1, 2, 3 or 4 ether moieties and which may also carry 1 or 2 radicals of the formula $R^2$—PEO—PAO—

PAO, PAO' are hydrophobic polyether moieties PAO as defined in claim 23,

PEO, PEO' are polyethyleneoxide moieties,

R is $C_1$-$C_{20}$ alkyl or a radical $R^2$—PEO—PAO—

$R^1$ is $C_1$-$C_{20}$ alkyl or $C_1$-$C_{20}$ alkylphenyl, $R^2$, $R^3$, $R^4$ are each independently hydrogen, $C_1$-$C_8$ alkyl, $C_1$-$C_8$ alkylcarbonyl, or benzyl, and $R^a$, $R^b$ are each independently hydrogen, $C_1$-$C_8$ alkyl or a radical $R^2$—PEO—PAO—.

6. The composition as claimed in claim 1, containing the compound C in an amount from 5 to 50% by weight, based on the total weight of the composition.

7. The composition as claimed in claim 1, comprising at least one non-polymeric surfactant in an amount from 0.1 to 10% by weight, based on the total weight of the composition.

8. The composition as claimed in claim 1, wherein the pesticide compound C is selected from fungicides, insecticides, acaricides, nematicides and herbicides.

9. The composition as claimed in claim 8, wherein the pesticide compound C is an insecticide compound.

10. The composition as claimed in claim 9, wherein the insecticide compound C is selected from compounds of the formula A

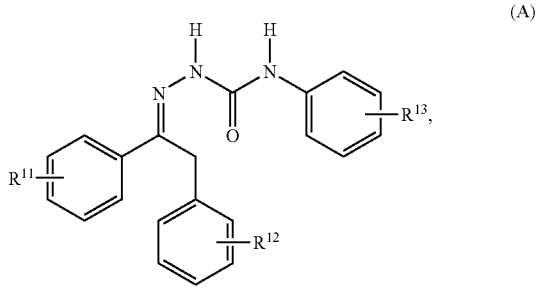

wherein $R^{11}$ and $R^{12}$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^{13}$ is $C_1$-$C_4$ alkoxy, $C_1$-$C_4$ haloalkyl or $C_1$-$C_4$ haloalkoxy.

11. The composition as claimed in claim 8, wherein the pesticide compound C is a fungicide compound.

12. An aqueous pesticide composition, which is obtained by dilution with water of a liquid pesticide concentrate composition as defined in claim 1, the dilution being at least 10 parts of water per 1 part of the liquid pesticide concentrate composition.

13. The composition as claimed in claim 12, wherein the non-ionic blockcopolymer and the at least one organic pesticide compound C form droplets having an average diameter, determined by dynamic light scattering method, from 10 to 300 nm.

14. A method of combating organisms that are harmful to plants, which comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of a composition as claimed in claim 12.

15. A method of combating organisms that are harmful to plants, which comprises contacting said harmful organisms, their habit, breeding ground, food supply, plant, seed, soil, area, material or environment in which the harmful organisms are growing or may grow, or the materials, plants, seeds, soils, surfaces or spaces to be protected from attack or infestation by harmful organisms with an effective amount of a composition as claimed in claim 13.

16. A method for protecting crops from attack or infestation by harmful organisms which comprises contacting a crop with an effective amount of a composition as claimed in claim 12.

17. A method for protecting crops from attack or infestation by harmful organisms which comprises contacting a crop with an effective amount of a composition as claimed in claim 13.

18. A method for protecting seeds from attack or infestation by harmful organisms which comprises contacting a seed with an effective amount of a composition as claimed in claim 12.

19. A method for protecting seeds from attack or infestation by harmful organisms which comprises contacting a seed with an effective amount of a composition as claimed in claim 13.

20. A liquid pesticide concentrate composition, comprising:
a) 1 to 60% by weight, based on the total weight of the composition, of at least one organic pesticide compound C having a water solubility of not more than 5 g/l at 25° C./1013 mbar,
b) 10 to 80% by weight, based on the total weight of the composition, of at least one organic solvent S having a water solubility of at least 50 g/l at 25° C./1013 mbar, and which is capable of dissolving the pesticide compound C,
c) from 15 to 50% by weight, based on the total weight of the composition, of at least one non-ionic blockcopolymer P comprising at least one polyethyleneoxide moiety PEO and at least one polyether moiety PAO consisting of repeating units derived from $C_3$-$C_{10}$-alkyleneoxides and/or styrene oxide, wherein the weight ratio of PEO moieties to POA moieties in the non-ionic blockcopolymer ranges from 3:7 to 7:3, and wherein the non-ionic blockcopolymer has a number average molecular weight $M_N$ ranging from 2,500 to 100,000 Dalton; and d) optionally from 0.1 to 10% by weight, based on the total weight of the composition, of one or more non-polymeric surfactants, e) wherein the weight ratio of the non-ionic blockcopolymer to the organic pesticide compound P:C is from 0.6:1 to 10:1 and wherein the components a), b), c) and optionally d) make up at least 95% of the composition, provided that if water is present in the composition, the weight ratio of water to solvent S does not exceed 1:5.

21. The composition as claimed in claim 20, wherein the non-ionic blockcopolymer has a number average molecular weight $M_N$ ranging from 2,500 to 50,000 Dalton.

22. The composition as claimed in claim 20, wherein the PEO and the PAO moieties make up at least 80% by weight of the non-ionic blockcopolymer P.

23. The composition as claimed in claim 20, wherein the pesticide compound C is selected from fungicides, insecticides, acaricides, nematicides and herbicides.

24. The composition as claimed in claim 20, wherein the pesticide compound C is selected from an insecticide compound.

25. The composition as claimed in claim 20, wherein the insecticide compound C is selected from compounds of the formula A

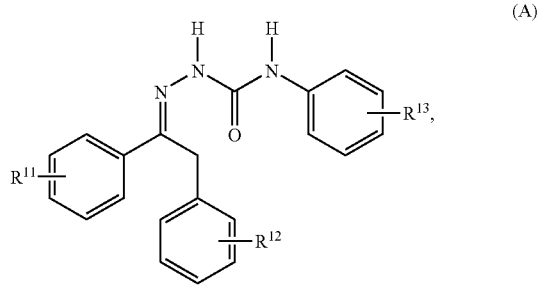

wherein $R^{11}$ and $R^{12}$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^{13}$ is $C_1$-$C_4$ alkoxy, $C_1$-$C_4$ haloalkyl or $C_1$-$C_4$ haloalkoxy.

26. A liquid pesticide concentrate composition, comprising:

a) 1 to 60% by weight, based on the total weight of the composition, of at least one organic pesticide compound C having a water solubility of not more than 5 g/l at 25° C./1013 mbar, b) 10 to 80% by weight, based on the total weight of the composition, of at least one organic solvent S having a water solubility of at least 50 g/l at 25° C./1013 mbar, and which is capable of dissolving the pesticide compound C, c) from 15 to 50% by weight, based on the total weight of the composition, of at least one non-ionic blockcopolymer P comprising at least one polyethyleneoxide moiety PEO and at least one polyether moiety PAO consisting of repeating units derived from $C_3$-$C_{10}$-alkyleneoxides and/or styrene oxide, wherein the weight ratio of PEO moieties to POA moieties in the non-ionic blockcopolymer ranges from 3:7 to 7:3, and wherein the non-ionic blockcopolymer has a number average molecular weight $M_N$ ranging from 2,500 to 100,000 Dalton; and d) optionally, comprising less than 0.1% non-polymeric surfactant, based on the total weight of composition, e) wherein the weight ratio of the non-ionic blockcopolymer to the organic pesticide compound P:C is from 0.6:1 to 10:1 and wherein the components a), b), c) and optionally d) make up at least 95% of the composition, provided that if water is present in the composition, the weight ratio of water to solvent S does not exceed 1:5.

27. The composition as claimed in claim 26, wherein the non-ionic blockcopolymer has a number average molecular weight $M_N$ ranging from 2,500 to 50,000 Dalton.

28. The composition as claimed in claim 26, wherein the PEO and the PAO moieties make up at least 80% by weight of the non-ionic blockcopolymer P.

29. The composition as claimed in claim 26, wherein the pesticide compound C is selected from fungicides, insecticides, acaricides, nematicides and herbicides.

30. The composition as claimed in claim 26, wherein the pesticide compound C is selected from an insecticide compound.

31. The composition as claimed in claim 26, wherein the insecticide compound C is selected from compounds of the formula A

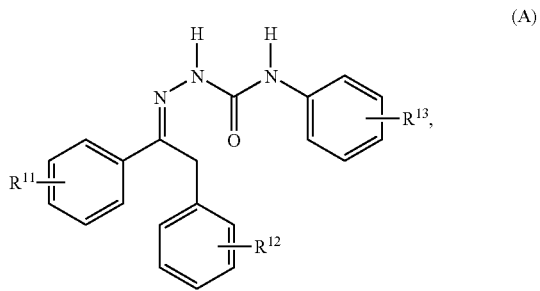

wherein $R^{11}$ and $R^{12}$ are each independently hydrogen, halogen, CN, $C_1$-$C_4$ alkyl, $C_1$-$C_4$ alkoxy, $C_1$-$C_4$ haloalkyl or $C_1$-$C_4$ haloalkoxy and $R^{13}$ is $C_1$-$C_4$ alkoxy, $C_1$-$C_4$ haloalkyl or $C_1$-$C_4$ haloalkoxy.

* * * * *